US008618320B2

(12) United States Patent
Zhang et al.

(10) Patent No.: US 8,618,320 B2
(45) Date of Patent: Dec. 31, 2013

(54) LEWIS ACID CATALYZED HALOGENATION OF ACTIVATED CARBON ATOMS

(75) Inventors: Yanhua Zhang, Hanover, NH (US); Hisashi Yamamoto, Chicago, IL (US); Kazutaka Shibatomi, Hiroshima (JP)

(73) Assignee: Japan Science and Technology Agency, Saitama (JP)

( * ) Notice: Subject to any disclaimer, the term of this patent is extended or adjusted under 35 U.S.C. 154(b) by 26 days.

(21) Appl. No.: 13/404,364

(22) Filed: Feb. 24, 2012

(65) Prior Publication Data
US 2012/0157691 A1 Jun. 21, 2012

Related U.S. Application Data

(60) Division of application No. 12/040,435, filed on Feb. 29, 2008, now abandoned, and a continuation-in-part of application No. PCT/US2006/034066, filed on Aug. 31, 2006.

(60) Provisional application No. 60/713,904, filed on Sep. 2, 2005.

(51) Int. Cl.
*C07F 7/12* (2006.01)
*C07F 7/08* (2006.01)

(52) U.S. Cl.
USPC .......................................... 556/476; 556/488

(58) Field of Classification Search
USPC ................................................. 556/476, 488
See application file for complete search history.

(56) References Cited

U.S. PATENT DOCUMENTS

| 4,740,629 A * | 4/1988 | Brackenridge et al. ....... 568/639 |
| 5,041,687 A * | 8/1991 | McKinnie et al. ............ 568/592 |
| 5,055,235 A | 10/1991 | Brackenridge et al. |
| 5,059,409 A | 10/1991 | Hung |
| 5,364,993 A | 11/1994 | Zhang et al. |
| 5,900,029 A | 5/1999 | Belmont et al. |
| 6,472,345 B2 * | 10/2002 | Hintermann et al. ......... 502/227 |
| 7,271,302 B1 | 9/2007 | Fabian et al. |
| 2005/0244644 A1 | 11/2005 | Hampden-Smith et al. |

FOREIGN PATENT DOCUMENTS

| JP | 41-11975 | 6/1941 |
| JP | 64/63540 | 3/1989 |
| JP | 5-246912 | 9/1993 |
| JP | 2002-145810 | 5/2002 |
| JP | 2003-510298 | 3/2003 |

OTHER PUBLICATIONS

Hauser, Charles et al. (J. Amer. Chem. Soc. (1952) 74; p. 5091-5096).*

Shimizu, Sumio et al. (Tetrahedron (1989), 45 (3); p. 637-642).*
Aramata, A. et al.: Ligand grafting method for immobilization of metal complexes on a carbon electrode Thin Solid Films, vol. 424, 2003 pp. 239-246.
Meijer, M. D. et al: "Methanofullerene-Based Palladium Bis(Amino)Aryl Complexes and Application in Lewis Acid Catalysis" Organometallics, vol. 20, No. 19, (Sep. 17, 2001), pp. 3993-4000.
Prakash et al., $N$-Halosuccinimide/$BF_3$—$H_2O$, Efficient Electrophilic Halogenating Sysets for Aromatics, J. Am. Chem. Soc. 2004,126,15770-15776.
Rajagopal et al., "Regioselective side-chain as well as nuclear monobromination of aromatic subsstrates with N-bromosuccinimide using phosphotungstic acid supported on zirconia a heterogeneous catalyst" Journal of Molecular Catalysis A: Chemical, vol. 210(2004); p. 165-169.).
Schmid, H.: "Bromierungen mit Brom-succinimid bei Gegenwart von Katalysatoren, II" Helv. Chemica Acta, vol. XXIX,1946, pp. 1144-1151.
Tanemura et al., "Halogenation of Aromatic compounds $N$-chloro-, $N$-bromo-, and $N$-iodosuccinimide", Chemistry Letters 2003,32(10),932-3.
Zanka et al., "Practical and Efficient Chlorination of Deactivated Anilines and Anilides with NCS in 2- Propanolo"Synlett 1999,12,1984-6.
Zhang et al., "Lewis Acid-Mediated Selective Chlorinations of Silyl Enolate" J. Am. Chem. Soc. 2004, 126, 15038-15039.
Zhang, Y. et al.: "Lewis Acid catalyzed highly selective halogenation of aromatic compounds" Synlett, No. 18, (Oct. 10, 2005), pp. 2837-2842.
International Search Report and Written Opinion Auq, 27-2007.
Supplementary European Search Report Jul. 1, 2009.
Excerpt translation of Office Action issued in Japanese Patent Application No. 2008-529282, providing statement of relevance of non-English documents provided herewith, (2008).
Hauser, Charles, R., et al., "Preparation and reactions of α-Halo Derivatives of Certain Tetra-substituted Hydrocarbon Silanes. Grignard Synthesis of Some Silyl Compounds", Journal of the American Chemical Society, Oct. 20, 1952, pp. 5091-5096, vol. 74.
Shimizu, Sumio et al., "The Fluoride-induced reaction of phenylthio-methylthio- and methoxy-subtituted silylmethylazoles with carbonyl compounds", Tetrahedron, 1989, pp. 637-642, vol. 45, No. 3.

* cited by examiner

*Primary Examiner* — Noble Jarrell
*Assistant Examiner* — Valerie Rodgriguez-Garcia
(74) *Attorney, Agent, or Firm* — Brinks Gilson & Lione

(57) ABSTRACT

A practical and efficient method for halogenation of activated carbon atoms using readily available N-haloimides and a Lewis acid catalyst has been disclosed. This methodology is applicable to a range of compounds and any halogen atom can be directly introduced to the substrate. The mild reaction conditions, easy workup procedure and simple operation make this method valuable from both an environmental and preparative point of view.

3 Claims, 1 Drawing Sheet

LEWIS ACID CATALYZED HALOGENATION OF ACTIVATED CARBON ATOMS

RELATED APPLICATIONS

This application is a divisional of U.S. application Ser. No. 12/040,435, filed Feb. 29, 2008, which application is a continuation-in-part of Patent Cooperation Treaty International Application No. PCT/US2006/034066, filed Aug. 31, 2006, which claims priority to U.S. provisional application Ser. No. 60/713,904 filed Sep. 2, 2005, the entire disclosures of which are hereby incorporated by reference.

BACKGROUND

Halogenation of activated carbon atoms is a highly useful reaction for the synthesis of natural products and pharmaceutically important compounds. Aromatic compounds are examples of compounds with activated carbon atoms. Aryl fluorides and chlorides are found in many natural products and pharmaceutical compounds. Aryl bromides and iodides are important building blocks in organic syntheses because of their utility in carbon-carbon bond forming reactions. For example, aryl bromides and iodides are precursors to numerous organometallic species that are used in organic synthesis. Organometallic species and aryl bromides and iodides or benzyl bromides or iodides are useful in cross coupling reactions, in particular, transition metal catalyzed cross coupling reactions that can furnish complex molecules under mild reaction conditions.

Classical reagents for the direct introduction of halogen atoms at an activated carbon atom are bromine, chlorine and iodine, for example. These reagents have a number of drawbacks including toxicity, high reactivity, corrosiveness, non-selectivity particularly in molecules with complex and sensitive functionality, as well as the fact that only half of the halogen in the reagent is consumed. In addition, the reaction product mixtures arising from these reagents can lead to high levels of toxic and corrosive waste, as well as purification difficulties. Halogenation of aromatic compounds is disclosed in Prakash, G. K. S., Mathew, T., Hoole, D., Esteves, P. M. *J. Am. Chem. Soc.* 2004, 126, 15770; Tanemura, K., Suzuki, T., Nishida, Y.; Satsumabayashi, K., Horaguchi, T. *Chem. Lett.* 2003, 32, 932; and Zanka, A., Kubota, A. *Synlett* 1999, 12, 1984.

In terms of ease of handling, haloimides are ideal halogenating reagents. For example, NBS, NIS, NCS and NFSI are solids that are non-corrosive, nonhydroscopic, and mild reagents that are easily handled under standard conditions. Previous attempts to employ these reagents for aromatic halogenation, however, have usually required severe reaction conditions to activate or enhance the halogenating ability of these compounds. For example, previous attempts employed highly acidic solutions, large amounts of catalyst and/or high temperatures.

It is desirable to have new methods for the halogenation of activated carbon atoms which are mild and tolerate complex functionality, particularly in the synthesis of complex organic molecules such as natural and pharmaceutical products.

BRIEF SUMMARY

In one embodiment of the present invention, methods of halogenating an activated carbon atom in the presence of a Lewis acid are provided. The halogenation method comprises reacting a material comprising an activated carbon atom with a halogen donor in the presence of a catalytic amount of the Lewis acid. The activated carbon atom is an aromatic carbon atom, a carbon atom alpha to an aromatic ring, or a carbon atom alpha to a silicon atom. The halogen donor is selected from the group consisting of N-bromosuccinimide, N-iodosuccinimide, N-chlorosuccinimide and N-fluorobenzenesulfonimide. In some aspects the Lewis acid comprises a metal selected from the group consisting of Zr, Fe, and Al.

In another embodiment of the present invention a functionalized elemental carbon material is provided. The functionalized elemental carbon material is prepared by reacting elemental carbon comprising an aromatic carbon compound with a halogen donor in the presence of a catalytic amount of the Lewis acid to form halogenated elemental carbon. In some aspects, the functionalized elemental carbon material is a catalyst, prepared by the steps further comprising coupling a functional group to the halogenated elemental carbon to form a functionalized elemental carbon; and complexing a metal to the functionalized elemental carbon. In some aspects, the preparation of the functionalized elemental carbon material further comprises reacting the elemental carbon with a halogen donor in the presence of a catalytic amount of a Lewis acid. In some aspects the elemental carbon is graphite or charcoal. In other aspects the functional group comprises a pyridyl ring.

DETAILED DESCRIPTION OF THE DRAWINGS AND THE PRESENTLY PREFERRED EMBODIMENTS

Abbreviations and Definitions

Figure 1:
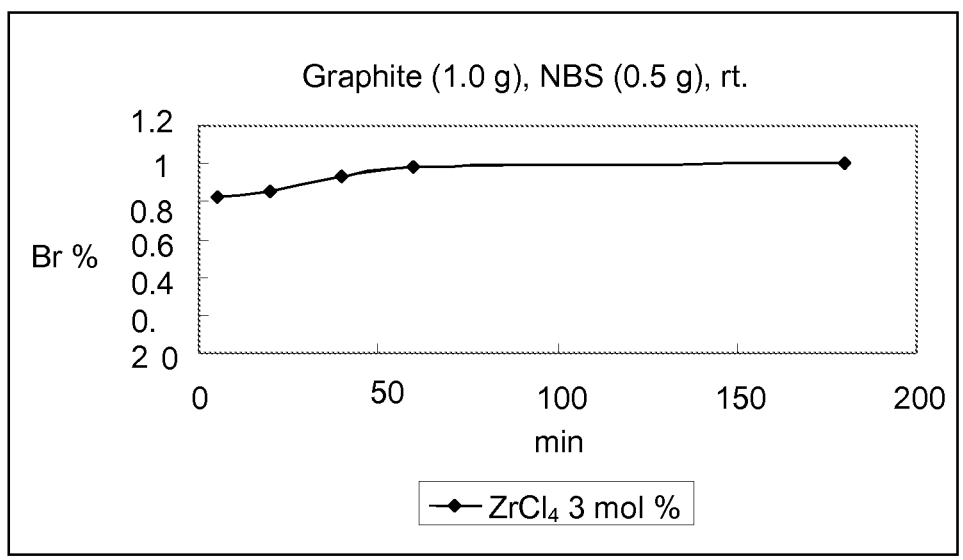
FIG. 1 is a graph depicting the bromination of graphite.

When describing the compounds, compositions, methods and processes of this invention, the following terms have the following meanings, unless otherwise indicated.

"Activated carbon atom" as used herein, is defined as a carbon atom of an aromatic ring, a carbon atom alpha to an aromatic ring, or a carbon atom alpha to a heteroatom.

"Alkene" or "olefin" refers to an unsaturated hydrocarbon group which may be linear, cyclic or branched or a combination thereof. These groups have at least 1 double bond, but can also include 2 or more double bonds. In addition, these groups can be substituted or unsubstituted. Possible substituents include hydrogen, alkyl, cycloalkyl, hydroxy, alkoxy, amino, alkylamino, halogen, heterocyclyl, aryl, heteroaryl, arylalkyl, O-silyl, and halogen. Alkene groups with 2 to 20 carbon atoms are preferred. Alkene groups with 2 to 16 carbon atoms are more preferred. Examples of alkene groups include ethenyl, n-propenyl, isopropenyl, n-but-2-enyl, n-hex-3-enyl and the like.

"Alkoxy" refers to those alkyl groups, having from 1 to 10 carbon atoms, attached to the remainder of the molecule via an oxygen atom. Alkoxy groups with 1-8 carbon atoms are preferred. The alkyl portion of an alkoxy may be linear, cyclic, or branched or a combination thereof. In addition, these groups can be substituted or unsubstituted. Examples of alkoxy groups include methoxy, ethoxy, isopropoxy, butoxy, cyclopentyloxy, and the like. An alkoxy group can also be represented by the following formula: —OR', where R' is the "alkyl portion" of an alkoxy group.

"Alkyl" by itself or as part of another substituent refers to a hydrocarbon group which may be linear, cyclic, or branched or a combination thereof having from 1 to 10 carbon atoms (preferably 1 to 8 carbon atoms). Thus, as defined herein, alkyl includes "cycloalkyl". In addition, these groups can be substituted or unsubstituted. Examples of alkyl groups include methyl, ethyl, n-propyl, isopropyl, n-butyl, t-butyl, isobutyl, sec-butyl, cyclohexyl, cyclopentyl, (cyclohexyl)methyl, cyclopropylmethyl and the like.

"Alkylamino" by itself or as part of another substituent refers to those alkyl groups, having from 1 to 10 carbon atoms, attached to the remainder of the molecule via a nitrogen atom. Alkylamino groups with 1-8 carbon atoms are preferred. The alkyl portion of an alkylamino may be linear, cyclic, or branched or a combination thereof. Examples of alkylamino groups include methylamino, ethylamino, isopropylamino, butylamino, dimethylamino, methyl, isopropylamino and the like. An alkylamino group can also be represented by the following formulae: —NR'— or —NR'R", or —NHR', where R' and R" are alkyl.

"Aryl" by itself or as part of another substituent refers to an aromatic hydrocarbon group comprising a single ring or multiple fused rings with 5 to 14 carbon atoms (preferably 5 to 10 carbon atoms). Each aryl group can be fused to a cycloalkyl, heterocyclyl, heteroaryl, or aryl group. In addition, these groups can be substituted or unsubstituted. Examples of aryl groups include phenyl, naphthyl, anthracyl, 1,2,3,4-tetrahydro-naphthyl and the like.

"Arylalkyl" by itself or as part of another substituent refers to an aryl group, attached to the remainder of the molecule via an alkyl group. Such groups may have single or multiple substituents on either the aryl ring or on the alkyl side chain. In addition, these groups can be substituted or unsubstituted. Examples include benzyl, phenylethyl, styryl, 2-(4-methylphenyl)ethyl, triphenylmethanyl, and 2-phenylpropyl.

"Aryloxy" by itself or as part of another substituent refers to an aromatic hydrocarbon group comprising a single ring or multiple fused rings with 5 to 14 carbon atoms (preferably 5 to 10 carbon atoms) attached to the remainder of the molecule via an oxygen atom. Each aryl group can be fused to a cycloalkyl, heterocyclyl, heteroaryl, or aryl group. In addition, these groups can be substituted or unsubstituted. Examples of aryloxy groups include phenol, naphthanol, anthranol and the like. An aryloxy group can also be represented by the following formula: —OR', where R' is the "aryl portion" of an alkoxy group.

"Arylamino" by itself or as part of another substituent refers to an aromatic hydrocarbon group comprising a single ring or multiple fused rings with 5 to 14 carbon atoms (preferably 5 to 10 carbon atoms) attached to the remainder of the molecule via a nitrogen atom. Each aryl group can be fused to a cycloalkyl, heterocyclyl, heteroaryl, or aryl group. In addition, these groups can be substituted or unsubstituted. Examples of arylamino groups include phenylamino, naphthylamino, anthracylamino and the like. An arylamino group can also be represented by the following formulae: —NR'— or —NR'R", or —NHR', where at least one of R' or R" are aryl.

"Elemental carbon" as used herein, is a material consisting essentially of the element carbon. Elemental carbon has several allotropic forms including diamond, graphite, Ionsdaleite, C60, C540, C70, amorphous carbon and a carbon nanotube. Many of these forms comprise aromatic carbon ring systems including graphite and charcoal. Graphite and charcoal are preferred elemental carbons comprising an aromatic carbon compound.

"Halo" or "halogen", by itself or as part of a substituent refers to a chlorine, bromine, iodine, or fluorine atom. Additionally, terms such as "Haloalkyl" refer to a monohaloalkyl or polyhaloalkyl group, most typically substituted with from 1-3 halogen atoms. Examples include 1-chloroethyl, 3-bromopropyl, trifluoromethyl and the like.

"Heteroatom" refers to an atom other than carbon. Examples include nitrogen, oxygen, sulfur, phosphorus, silicon and the like.

The term "heteroalkyl," refers to a straight or branched chain group consisting of 1 to 10 carbon atoms (preferably 1 to 8 carbon atoms) and from one to three heteroatoms selected from the group consisting of O, N, P, Si and S, and wherein the nitrogen, sulfur and phosphorus atoms may optionally be oxidized. The heteroatom(s) O, N, P and S may be placed at any interior position of the heteroalkyl group. The heteroatom Si may be placed at any position of the heteroalkyl group, including the position at which the alkyl group is attached to the remainder of the molecule. Examples include —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$—S(O)—CH$_3$, —CH$_2$—CH$_2$—S(O)$_2$—CH$_3$, —CH=CH—O—CH$_3$, —Si(CH$_3$)$_3$, —CH$_2$—CH=N—OCH$_3$, and —CH=CH—N(CH$_3$)—CH$_3$. Up to two heteroatoms may be consecutive, such as, for example, —CH$_2$—NH—OCH$_3$ and —CH$_2$—O—Si(CH$_3$)$_3$.

"Heteroaryl" refers to an aromatic hydrocarbon group having at least one heteroatom and comprising a single ring or multiple fused rings. A heteroaryl group preferably has 3 to 14 members (preferably 3 to 10 members). Each heteroaryl group can be fused to a cycloalkyl, heterocyclyl, heteroaryl, or aryl group. Each heteroaryl must contain at least one heteroatom (typically 1 to 5 heteroatoms) selected from the group consisting of nitrogen, oxygen and sulfur. Preferably, a heteroaryl group contains 0-3 nitrogen atoms, 0-1 oxygen atoms and 0-1 sulfur atoms. In addition, these groups can be substituted or unsubstituted. Examples of heteroaryl groups include pyrrolyl, imidazolyl, oxazolyl, furanyl, triazolyl, tetrazolyl, oxadiazolyl, pyrazolyl, isoxazolyl, pyridinyl, pyrazinyl, pyridazinyl, pyrimidinyl, triazinyl, indolyl, thiophenyl, benzothiophenyl, benzofurayl, benzimidazolyl, benzopyrazolyl, quinolinyl, isoquinolinyl, quinazolinyl, quinoxalinyl and the like. Heteroaryl groups can be unsubstituted or substituted. For substituted heteroaryl groups, the substitution may be on a carbon or heteroatom. For example, when the substitution is =O, the resulting group may be a N-oxide (—N(O)—) when the substitution is on a nitrogen.

"Heterocyclyl" refers to a saturated or unsaturated non-aromatic group containing at least one heteroatom and having 3 to 10 members (preferably 3 to 7 carbon atoms). Each heterocyclyl may have one or more rings. When multiple rings are present in a heterocyclyl, they can be fused together or linked covalently. Each heterocyclyl can be fused to a cycloalkyl, heterocyclyl, heteroaryl, or aryl group. Each heterocyclyl must contain at least one heteroatom (typically 1 to 5 heteroatoms) selected from nitrogen, oxygen or sulfur. Preferably, a heterocyclyl group contains 0-3 nitrogen atoms and 0-1 oxygen atoms. In addition, these groups can be substituted or unsubstituted. Examples of saturated and unsaturated heterocyclyl groups include pyrrolidinyl, imidazolidinyl, pyrazolidinyl, piperidinyl, 1,4-dioxanyl, morpholinyl, piperazinyl, 3-pyrrolinyl and the like. Heterocyclyl groups can be unsubstituted or substituted. For substituted heterocyclyl groups, the substitution may be on a carbon or heteroatom. For example, when the substitution is =O, the resulting group may have either a carbonyl (—C(O)—) or a N-oxide (—N(O)—).

"Laser" refers to a device which emits coherent light radiation in a narrow, low-divergence monochromatic beam with a well-defined wavelength. The light radiation may be photons of electromagnetic energy including the visible, infrared and ultravioulet spectrums. Examples of lasers include visible light lasers, infrared lasers, ultraviolet lasers, and the like. The laser light is a beam with a well-defined wavelength. In contrast, incandescent light has a wide spectrum of wavelengths.

"Lewis acid" refers to any species with a vacant orbital, in contrast to a "Lewis base," which refers to a compound with an available pair of electrons, either unshared or in a π-orbital. Typically, a Lewis acid refers to a compound containing an element that is two electrons short of having a complete valence shell. As used herein, the term "Lewis acid" does not include protic acids.

"Light" refers to electromagnetic radiation of a wavelength that is visible to the human eye (about 400-700 nm) or near the visible region such as the infrared and ultraviolet region. Preferably, light is visible to the human eye. Light refers to incandescent light and laser light.

"Substituted" means that the moiety contains at least one, preferably 1 to 3 substituent(s). Suitable substituents include halogen, $C_{1-8}$ alkyl, $C_{1-8}$ heteroalkyl, $C_{1-8}$ haloalkyl, —CN, —NO$_2$, —OR', —OC(O)R', —CO$_2$R', —C(O)R', —C(O)NR'R", —OC(O)NR'R", —NR'''C(O)R', —NR'''C(O)NR'R", —NR'R", —NR'''CO$_2$R", —SR', —S(O)R', —S(O)$_2$R', —S(O)$_2$NR'R", —NR'''S(O)$_2$R", $C_{2-8}$ alkenyl, $C_{2-8}$ alkynyl, 3- to 10-membered heterocyclyl, $C_{6-10}$ aryl, and 5- to 10-membered heteroaryl;

wherein R', R" and R'" are each independently selected from the group consisting of hydrogen, $C_{1-8}$ alkyl, $C_{1-8}$ heteroalkyl, $C_{2-8}$ alkenyl, $C_{2-8}$ alkynyl, $C_{6-10}$ aryl, 5- to 10-membered heteroaryl, and 3- to 10-membered heterocycle; R' and R" may together with the atom(s) to which they are attached, form a substituted or unsubstituted 5-, 6-, or 7-membered cycloalkyl or heterocyclyl.

Examples of substituted substituents include alkylamino, dialkylamino, alkylaryl, aralkyl, and the like. When 3- to 10-membered heterocyclyl, $C_{6-10}$ aryl, 5- to 10-membered heteroaryl, and cycloalkyl are substituents, these groups can be linked through a single bond or these groups can be fused. For example when benzene is substituted with a phenyl group, which is an example of a $C_{6-10}$ aryl group, the result can be biphenyl or naphthalene.

Halogenation of Activated Carbon Atoms

A simple and efficient procedure for the halogenation of activated carbon atoms is disclosed herein.

As used herein, halogenation of activated carbon atoms is defined as the process of forming a carbon-halogen bond in a compound having an activated carbon atom. The activated carbon atom has a carbon-hydrogen bond which may be transformed to a carbon-halogen bond. An activated carbon atom is defined as a carbon atom of an aromatic ring, a carbon atom alpha to an aromatic ring, or a carbon atom alpha to a heteroatom.

As used herein, the term aromatic ring or aromatic compound encompasses both aryls and heteroaryls. Examples of aromatic compounds include benzene, napthalene, anthracene, toluene, methylnaphthalene, methylanthracene, indole, furan, thiophene, 1,2,3,4-tetrahydro-naphthalene, 2,3-dihydrobenzofuran, indoline, 2,3-dihydrobenzothiophene, and the like. Aromatic compounds can be substituted or unsubstituted.

An example of a compound with a carbon atom alpha to an aromatic ring is toluene, wherein the position of the carbon atom alpha to the aromatic ring is often referred to as the benzylic position. It is to be understood that the aromatic ring may be aryl or heteroaryl. The carbon atom alpha to the aromatic ring may be part of a chain or ring which may be substituted or unsubstituted.

Another type of activated carbon is a carbon atom alpha to a heteroatom. A heteroatom refers to an atom other than carbon. Examples include nitrogen, oxygen, sulfur, phosphorus, silicon and the like. Examples of compounds comprising a heteroatom include silanes, ethers, sulfides, amines and the like. In the halogenation of carbon atoms alpha to a heteroatom, silanes are preferred compounds where the heteroatom is silicon.

Halogen Donors

The halogenation of activated carbon atoms is achieved using a Lewis acid catalyst and a halogen donor. A halogen donor is a compound that is capable of donating a halogen atom to the formation of a carbon-halogen bond, and is often referred to in the art as an electrophilic halogenating reagent. Halogen donor compounds within the scope of the present invention include any halogen containing compound whose ability to donate a halogen atom is enhanced in the presence of a Lewis acid catalyst. Suitable halogen donor compounds included haloimides which are defined as compounds including a "N—X" functionality, wherein the nitrogen atom is attached to two electron withdrawing groups, and X is a halogen. Examples of haloimide compounds include compounds with the following functional groups:

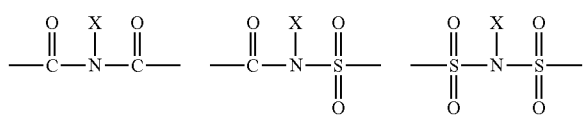

wherein X is halogen. Preferred haloimides are N-bromosuccinimide (NBS), N-iodosuccinimide (NIS), N-chlorosuccinimide (NCS) or N-fluorobenzene-sulfonimide (NFSI):

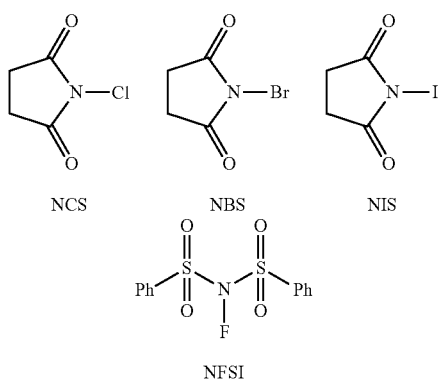

Other examples of haloimides include imidazolidine-2,4-diones, preferably 1,3-dihalo-5,5-dimethylimidazolidine-2,4-dione, more preferably 1,3-dibromo-5,5-dimethylimidazolidine-2,4-dione or 1,3-dichloro-5,5-dimethylimidazolidine-2,4-dione, most preferably 1,3-dibromo-5,5-dimethylimidazolidine-2,4-dione as shown below.

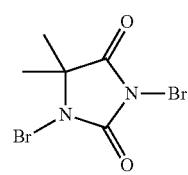

Without wishing to be bound by any theory of interpretation, it is believed that the reactivity of the haloimide compounds may be enhanced by preferential coordination of the Lewis acid catalyst with the oxygen of the carbonyl or sulfonyl moiety of the haloimide. For example, coordination of $ZrCl_4$ with the carbonyl oxygen of a halo-succinimide to increase the reactivity of halogen atom is illustrated below.

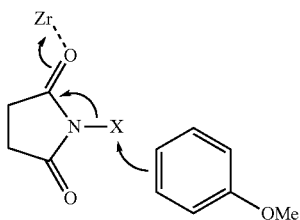

A specific halogen donor is selected based on the identity of the halogen that is desired in the halogenated aromatic compound. For example, if a chlorinated aromatic compound is desired, NCS would be a suitable halogen donor. If a brominated aromatic compound is desired, NBS would be suitable. If an iodinated or fluorinated aromatic compound is desired, NIS and NFSI, respectively, would be suitable.

In one embodiment, the halogen donor is N-bromosuccinimide.

In another embodiment, the halogen donor is N-fluorobenzene-sulfonimide.

In yet another embodiment, the halogen donor is 1,3-dibromo-5,5-dimethylimidazolidine-2,4-dione.

Lewis Acid Catalyst

The halogenation of an activated carbon atom further comprises a Lewis acid catalyst. The Lewis acid catalyst may comprise any Lewis acid which accelerates the reaction between the halogen donor compound and the activated carbon atom. The Lewis acid catalyst comprises a metal. Examples of metals include Al, B, Sn, Cs, transition metals, lanthanide metals, actinide metals and mixtures thereof. Preferably the metal is Al, Fe, or Zr. More preferably the metal is Zr.

The Lewis acid catalyst also comprises one or more ligands. Ligands may be mono- or multi-dentate, chiral or achiral. Examples of ligands include halogen, alkoxy, aryloxy, alkyamino, arylamino, olefin, phosphorous containing compounds, BINOL, tartrate, and the like. Chiral ligands according to the invention are moieties which possess chiral centers and exert facial selectivity of a reaction based on their chirality. A chiral center is, of course, an atom to which four different groups are attached; however, the ultimate criterion of chirality is nonsuperimposability on the mirror image.

Any Lewis acid catalyst which accelerates the reaction between the halogen donor compound and the activated carbon atom is suitable for use in the halogenation reaction of the present invention. Some Lewis acid catalysts are more preferable than others. $HfCl_4$, $TiCl_4$, and $ZnCl_2$ were found to be less than optimal catalysts in the halogenation reaction. Preferred Lewis acid catalysts include $ZrCl_4$, $FeCl_3$ and $AlCl_3$. More preferably, the Lewis acid comprises Zr. Most preferably, the Lewis acid catalyst is $ZrCl_4$. Zirconium tetrachloride is an ideal Lewis acid for this purpose, since it is known for its low toxicity.

The amount of Lewis acid catalyst used in the halogenation of an aromatic compound depends on a variety of factors. Generally, however, the Lewis acid catalyst is present in a catalytic amount, wherein a catalytic amount is defined as an amount sufficient to accelerate the reaction between the halogen donor compound and the starting material comprising the activated carbon atom. The catalytic amount of Lewis acid is less than 100 mole % relative to the starting material comprising the activated carbon atom, preferably from about 0.5 mole % to about 25 mole %, more preferably from about 0.5 mole % to 10 mole %, also more preferably about 5 mole %.

The halogenation of an activated carbon atom is carried out in the presence of light. Any suitable source of light which promotes the halogenation reaction may be employed. For example, light in the visible spectrum may be employed and may comprise a wide spectrum of wavelengths such as, for example incandescent light, or a narrow, well-defined wavelength such as laser light. Preferably laser light is employed, more preferably a green laser, even more preferably laser light with a wavelength of about 532 nm.

The halogenation of an activated carbon atom is carried out in a solvent, such as methylene chloride or ethyl ether. In a preferred embodiment, methylene chloride is employed as the solvent in the halogenations disclosed herein.

The halogenation of an activated carbon atom is carried out at a temperature range at or below the boiling point of the solvent. Preferably the reaction temperature is less than about 40° C., more preferably less than about 30° C. or less than about 20° C., even more preferably less than about 0° C. When a laser light is employed, the reaction temperature may be less than about 0° C., preferably less than about −30 about 0° C., more preferably less than about −60° C.

The halogenation of an activated carbon atom is carried out at atmospheric pressure. High pressure conditions including sealed tube reactions are not necessary to practice the present invention, and preferably are not used.

The yield of the halogenated product produced by the halogenation reaction of the present invention can vary depending on a variety of factors. For example, the choice and amount of the halogen donor and Lewis acid catalyst can affect the yield of the aromatic product. The yield of the halogenation reaction is preferably greater than 50%, preferably greater than 80%, more preferably greater than 90%, also more preferably greater than 95%. Where the halogenated product produced by the halogenation reaction of the present invention is chiral, the enantiomeric excess is preferably greater than 90%, more preferably greater than 95%, even more preferably greater than 99%.

Substrates for Halogenation

In one embodiment, the activated carbon atom is a carbon atom of an aromatic ring and the halogenation reaction can be represented as shown in Scheme 1.

Scheme 1

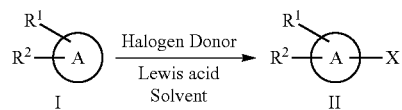

In each of formulae I and II, Ring A is an aryl or heteroaryl group.

The substituent $R^1$ is selected from the group consisting of —$OR^3$, —$NR^3R^4$, and —$SR^3$;

wherein $R^3$ and $R^4$ are each independently selected from the group consisting of hydrogen, $C_{1-8}$ alkyl, $C_{1-8}$ heteroalkyl, $C_{2-8}$ alkenyl, $C_{2-8}$ alkynyl, $C_{6-10}$ aryl, 5- to 10-membered heteroaryl, and 3- to 10-membered heterocycle; $R^3$ and $R^4$ may together with the atom(s) to which they are attached, form a 5-, 6-, or 7-membered cycloalkyl or heterocyclyl.

The substituent $R^2$ represents 0 to 5 substituents each independently selected from the group consisting of hydrogen, —OR$^3$, —NR$^3$R$^4$, —SR$^3$, C$_{1-8}$ alkyl, C$_{1-8}$ heteroalkyl, C$_{1-8}$ haloalkyl, C$_{2-8}$ alkenyl, C$_{2-8}$ alkynyl, 3- to 10-membered heterocyclyl, C$_{6-10}$ aryl, and 5- to 10-membered heteroaryl.

The substituent X in formula II, represents a halogen selected from the group consisting of chloro, bromo, iodo and fluoro.

In another embodiment, the halogenation reaction can be represented as shown in Scheme 2.

Scheme 2

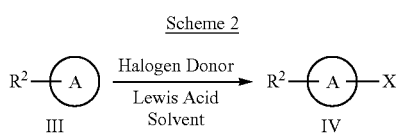

In each of formulae III and IV, R$^2$ is as defined for formula I, Ring A is heteroaryl. In formula IV, X is as defined for formula II.

In another embodiment, halogenation reaction can be represented as shown in Scheme 3.

Scheme 3

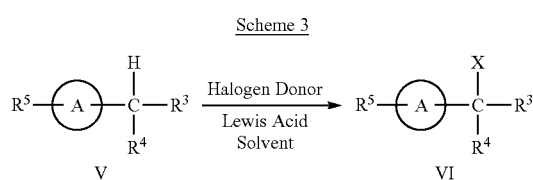

In each of formulae V and VI, R$^3$ and R$^4$, are as defined for formula I, and Ring A is an aryl or heteroaryl group. Preferably Ring A is aryl. In formula VI, X is as defined for formula II.

The substituent R$^5$ represents 0 to 5 substituents each independently selected from the group consisting of hydrogen and halogen.

Formula I and III are aromatic compounds, referred to herein as aromatic starting materials, that are converted to Formula II and IV, respectively, which are halogenated aromatic products. Formula V is an example of a compound with an activated carbon atom alpha to an aromatic ring which is converted to the halogenated product of Formula VI. Thus, Formula II, IV and VI are merely halogenated derivatives of Formula I, III, and V, respectively.

In an additional embodiment, the aromatic starting material and the halogenated aromatic product comprise Formulae Ia and IIa, respectively, as shown in Scheme 4.

Scheme 4

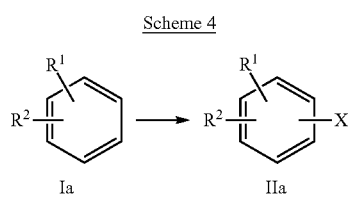

In another embodiment, the aromatic starting material and the halogenated aromatic product comprise Formulae Ib and IIb, respectively, as shown in Scheme 5.

Scheme 5

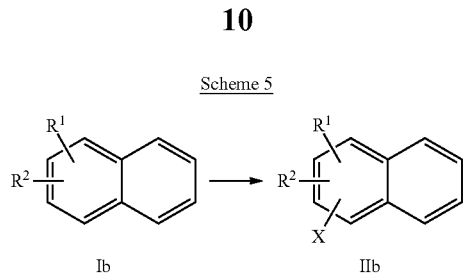

In one embodiment, the aromatic starting material and the halogenated aromatic product comprise Formulae IIIa and IVa, respectively, as shown in Scheme 6.

Scheme 6

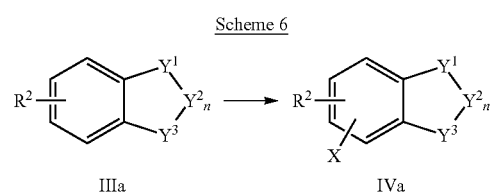

wherein:
X is as defined for formula II, and R$^2$ is as defined for formula I, with the proviso that R$^2$ represents 0 to 4 substituents;
Y$^1$ is selected from the group consisting of —NR$^3$—, —O—, and —S—;
Y$^2$ is each independently —CR$^3$R$^4$—;
Y$^3$ is selected from the group consisting of —NR$^3$—, —O—, —CR$^3$R$^4$— and —S—;
wherein R$^3$ and R$^4$ are defined as in formula I; and
n is 1, 2 or 3.

In a further embodiment, the aromatic starting material and the halogenated aromatic product comprise Formulae IIIb and IVb, respectively, as shown in Scheme 7, wherein R$^2$ and Y$^1$ are as defined as in formula IIIa, Scheme 6, and X is as defined for formula II.

Scheme 7

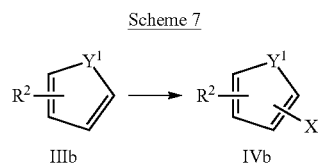

In one embodiment, the starting material and the halogenated product comprise Formulae Va and VIa, respectively, as shown in Scheme 8, wherein R$^3$, R$^4$, and R$^5$ are as defined for formula V, and X is as defined for formula II.

Scheme 8

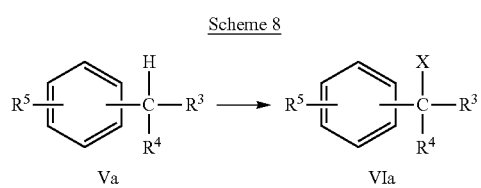

In one embodiment, the starting material and the halogenated product comprise Formulae Vb and VIb, respectively, as shown in Scheme 9, wherein $R^3$, $R^4$, and $R^5$ are as defined for formula V and X is as defined for formula II.

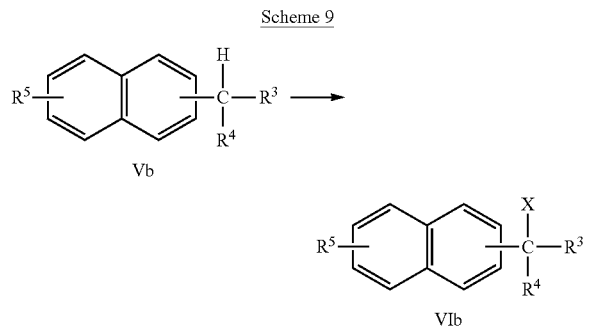

In another embodiment, the starting material and the halogenated product comprise Formulae Vc and VIc, respectively, as shown in Scheme 10, wherein $R^4$, and $R^5$ are as defined for formula V, and X is as defined for formula II.

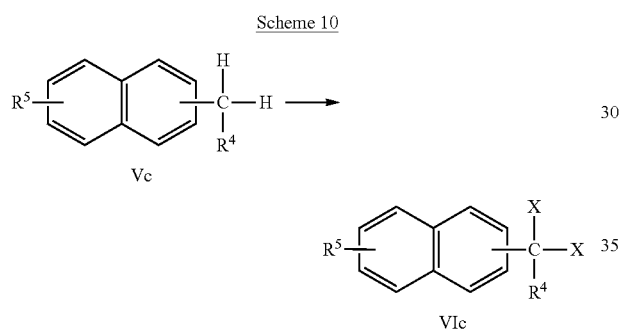

In another embodiment, the starting material and the halogenated product comprise Formulae Vd and VId, respectively, as shown in Scheme 11, wherein $R^5$ is as defined for formula V, and X is as defined for formula II.

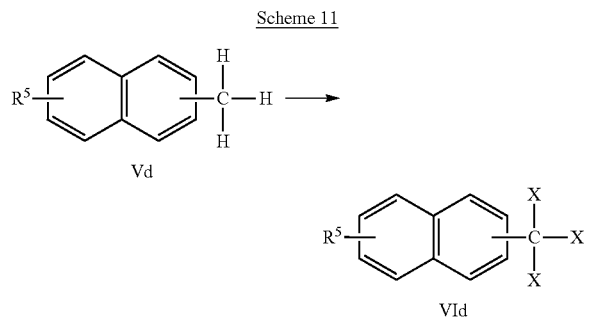

In another embodiment, the starting material and the halogenated product comprise Formulae VII and VIII, respectively, as shown in Scheme 12, wherein $R^3$ and $R^4$ are as defined for formula I, and X is as defined for formula II. The substituent $R^6$ is selected from the group consisting of —Si$(R^2)_3$, —OR$^3$, —NR$^3$R$^4$, and —SR$^3$.

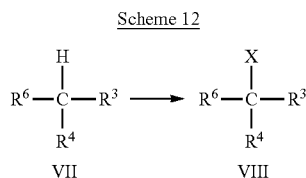

In another embodiment, the starting material and the halogenated product comprise Formulae VIIa and VIIIa, respectively, as shown in Scheme 13 wherein $R^2$, $R^3$, and $R^4$ are as defined for formula I, and X is as defined for formula II.

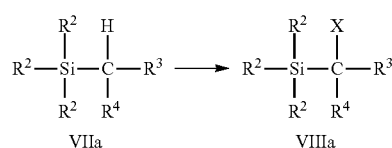

In another embodiment, the starting material and the halogenated product comprise Formulae VIIb and VIIIb, respectively, as shown in Scheme 14 wherein $R^2$, $R^3$, and $R^4$ are as defined for formula I, and X is as defined for formula II.

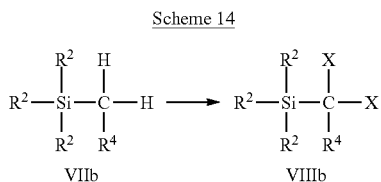

In another embodiment, the starting material and the halogenated product comprise Formulae VIIc and VIIIc, respectively, as shown in Scheme 15 wherein $R^2$, $R^3$, and $R^4$ are as defined for formula I, and X is as defined for formula II.

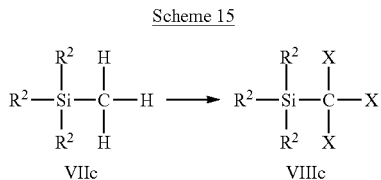

In another embodiment, the starting material may comprise an aromatic compound. Elemental carbon has several known allotropes including: diamond, graphite, Ionsdaleite, C60, C540, C70, amorphous carbon and a carbon nanotube. Many of these forms comprise aromatic groups. For example, graphite comprises broad flat sheets of hexagonal aromatic carbon rings. These sheets are stacked upon each other and are weakly bonded together. Charcoal comprises more than one allotrope, specifically, crystallites of graphite with varying amounts of amorphous carbon holding them together.

Material comprising aromatic rings are suitable substrates or starting materials in the halogenation methods of the present invention. In one embodiment, elemental carbon is the starting material. The starting material and the halogenated product comprise Formulae IX and X, respectively, as shown in Scheme 16, wherein X is as defined for formula II.

Scheme 16

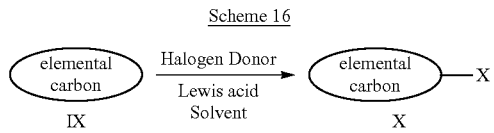

In another embodiment, the starting material and the halogenated product comprise Formulae IXa and Xa, respectively, as shown in Scheme 17 wherein X is as defined for formula II.

Scheme 17

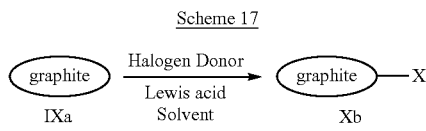

In another embodiment, the starting material and the halogenated product comprise Formulae IXb and Xb, respectively, as shown in Scheme 18 wherein X is as defined for formula II.

Scheme 18

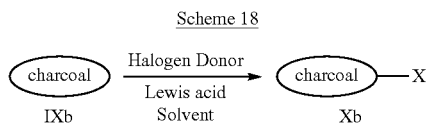

For the halogenation of materials comprising aromatic compounds such as elemental carbon, graphite and charcoal, it is to be understood that the material may comprise many activated carbon atoms which can be halogenated, and thus Schemes 16-18 in no way limit the number of halogen atoms that may be incorporated into such a material according to the methods of the present invention. Halogenated materials comprising aromatic compounds such as elemental carbon, graphite and charcoal may find application in catalysis, electronic and ionic conduction, adsorption, heat transfer and luminescence.

Without wishing to be bound by theory, the halogenation of elemental carbon comprising aromatic rings is believed to take place on the edges of the rings. For example, graphite is an extended sheet of carbon rings fused together. The halogenation is believed to take place on the edges of these sheets.

Preferred $R^1$ Groups.

In a preferred embodiment any of Schemes 1, 4, and 5, substituent X is located ortho to substituent $R^1$.

In a preferred embodiment, substituent X is located para to substituent $R^1$.

In a preferred embodiment for any of Schemes 1, 4, and 5, $R^1$ is —$OR^3$, more preferably —OMe or —OH.

In a preferred embodiment for any of Schemes 1, 4, and 5, $R^1$ is —$NR^3R^4$, more preferably —$NH_2$.

In a preferred embodiment for any of Schemes 1, 4, and 5, $R^1$ is —$SR^3$.

Preferred $R^2$ Groups.

In another preferred embodiment for any of Schemes 1-7 and 12-14, $R^2$ is selected from the group consisting of halogen, $C_{1-8}$ alkyl, $C_{1-8}$ heteroalkyl, $C_{1-8}$ haloalkyl, $C_{2-8}$ alkenyl, $C_{2-8}$ alkynyl, 3- to 10-membered heterocyclyl, $C_{6-10}$ aryl, and 5- to 10-membered heteroaryl.

In another embodiment for any of Schemes 1-7 and 12-14, $R^2$ is selected from the group consisting of $C_{1-8}$ alkyl, $C_{1-8}$ heteroalkyl and $C_{1-8}$ haloalkyl.

In another embodiment for any of Schemes 1-7 and 12-14, $R^2$ is $C_{1-8}$ alkyl.

In another embodiment for any of Schemes 1-7 and 12-14, $R^2$ is selected from the group consisting of $C_{2-8}$ alkenyl and $C_{2-8}$ alkynyl.

In another embodiment for any of Schemes 1-7 and 12-14, $R^2$ is selected from the group consisting of 3- to 10-membered heterocyclyl, $C_{6-10}$ aryl, and 5- to 10-membered heteroaryl.

Preferred $R^3$ and $R^4$ Groups.

In one embodiment for any of Schemes 1-10 and 12-14, $R^3$ and $R^4$ are each independently selected from the group consisting of hydrogen, $C_{1-8}$ alkyl, $C_{1-8}$ heteroalkyl, $C_{2-8}$ alkenyl, $C_{2-8}$ alkynyl, $C_{6-10}$ aryl, 5- to 10-membered heteroaryl, and 3- to 10-membered heterocycle; $R^3$ and $R^4$ may, together with the atom(s) to which they are attached, form a 5-, 6-, or 7-membered cycloalkyl or heterocyclyl.

In one embodiment for any of Schemes 1-10 and 12-14, $R^3$ and $R^4$ are each independently selected from the group consisting of hydrogen, $C_{1-8}$ alkyl, $C_{1-8}$ heteroalkyl, $C_{2-8}$ alkenyl, $C_{2-8}$ alkynyl, and 3- to 10-membered heterocycle; $R^3$ and $R^4$ may, together with the atom(s) to which they are attached, form a 5-, 6-, or 7-membered cycloalkyl or heterocyclyl.

In one embodiment for any of Schemes 1-10 and 12-14, $R^3$ and $R^4$ are each independently selected from the group consisting of hydrogen, $C_{1-8}$ alkyl, $C_{1-8}$ heteroalkyl, and 3- to 10-membered heterocycle; $R^3$ and $R^4$ may, together with the atom(s) to which they are attached, form a 5-, 6-, or 7-membered cycloalkyl or heterocyclyl.

In one embodiment for any of Schemes 1-10 and 12-14, $R^3$ and $R^4$ are each independently selected from the group consisting of hydrogen, $C_{1-8}$ alkyl, and $C_{1-8}$ heteroalkyl.

In one embodiment for any of Schemes 1-10 and 12-14, $R^3$ and $R^4$ are each independently selected from the group consisting of hydrogen, and $C_{1-8}$ alkyl.

In one embodiment for any of Schemes 1-10 and 12-14, $R^3$ and $R^4$ are each independently selected from the group consisting of hydrogen, $C_{6-10}$ aryl, and 5- to 10-membered heteroaryl.

In one embodiment for any of Schemes 1-10 and 12-14, $R^3$ and $R^4$ are each independently selected from the group consisting of hydrogen and $C_{6-10}$ aryl.

Preferred $R^5$ Groups.

In one embodiment for any of Schemes 3, or 8-11, $R^5$ is hydrogen.

In another embodiment for any of Schemes 3, or 8-11, at least one $R^5$ is halogen, and the remaining $R^5$ are hydrogen.

In another embodiment for any of Schemes 3, or 8-11, at least two $R^5$ are halogen, and the remaining $R^5$ are hydrogen.

Preferred X Groups.

In another embodiment for any of Schemes 1-14, X is bromo.

In another embodiment for any of Schemes 1-14, X is chloro.

In another embodiment for any of Schemes 1-14, X is iodo.

In another embodiment for any of Schemes 1-11, X is fluoro.

Preferred Y Groups.

In one embodiment for any of Schemes 2, 6, or 7, $Y^1$ is —$NR^3$. More preferably, $Y^1$ is —NH.

In another embodiment for any of Schemes 2, 6, or 7, $Y^1$ is —O—.

In another embodiment for any of Schemes 2, 6, or 7, $Y^1$ is —S—.

In one embodiment of Formula IIIa, $Y^2$ and $Y^3$ are each independently —$CR^3R^4$.

In one embodiment of Formula IIIa, $Y^2$ and $Y^3$ are each independently —$CR^3R^4$; and n is 1.

In another embodiment of Formula IIIa, $Y^1$ is —O—, $Y^2$ and $Y^3$ are each —$CH_2$—, and n is 1.

Halogenated Elemental Carbon

In one embodiment, a halogenated elemental carbon is provided prepared by the steps of reacting elemental carbon comprising an aromatic carbon compound with a halogen donor in the presence of a catalytic amount of the Lewis acid to form halogenated elemental carbon; wherein the halogen donor is selected from the group consisting of N-bromosuccinimide, N-iodosuccinimide, N-chlorosuccinimide and N-fluorobenzene-sulfonimide.

The elemental carbon may be graphite or charcoal. The Lewis acid may comprise a metal selected from the group consisting of Zr, Fe, and Al, preferably Zr. Preferably the Lewis acid is $ZrCl_4$.

Catalysts on Elemental Carbon Support

In one embodiment, a catalyst is provided which is prepared by the steps of halogenating elemental carbon comprising an aromatic carbon compound to form halogenated elemental carbon; coupling a functional group to the halogenated elemental carbon to form a functionalized elemental carbon; complexing a metal to the functionalized elemental carbon. Additionally, the catalyst may be prepared by reacting the elemental carbon with a halogen donor in the presence of a catalytic amount of a Lewis acid. In some aspects the Lewis acid is Zr, Fe or Al, preferably Zr. Preferably the Lewis acid is $ZrCl_4$.

Elemental carbon is a material consisting essentially of the element carbon. Elemental carbon has several allotropic forms including diamond, graphite, Ionsdaleite, C60, C540, C70, amorphous carbon and a carbon nanotube. Many of these forms comprise aromatic carbon ring systems including graphite and charcoal. Graphite and charcoal are preferred elemental carbons comprising an aromatic carbon compound.

Elemental carbon comprising an aromatic carbon compound can be halogenated according to the methods of the present invention. The halogenated elemental carbon may be further functionalized by coupling a functional group to the halogenated elemental carbon. Any functional group which may be coupled to the halogenated elemental carbon and which can act as a ligand for transition metal catalysts is suitable. A functional group comprising a pyridyl ring is preferred. The pyridyl functional group may be coupled via any suitable position to the halogenated elemental carbon which allows the pyridyl nitrogen to coordinate to a transition metal. The pyridyl ring may be unsubstituted or substituted. In one aspect, the pyridyl functional group is a bipyridyl ring system.

The functionalized elemental carbon may act as a ligand for a transition metal. Any transition metal which can complex with the functionalized elemental carbon is suitable. Palladium is a preferred transition metal. Either Pd(0) or Pd(II) oxidation state may be used. Sources of Pd(0) and Pd(II) are known to one skilled in the art, including, for example $Pd(Ph_3)_4$, $Pd(OAc)_2$, and $PdCl_2$. Complexing the transition metal to the functionalized elemental carbon comprises contacting the transition metal and the functionalized elemental carbon and may further included heating or concentrating the mixture.

In one aspect of the catalyst, the elemental carbon is graphite or charcoal; wherein the halogen donor is selected from the group consisting of N-bromosuccinimide, N-iodosuccinimide, N-chlorosuccinimide and N-fluorobenzene-sulfonimide; and wherein the Lewis acid comprises a metal selected from the group consisting of Zr, Fe, and Al.

Method of Halogenation

In one embodiment, a method of halogenating an activated carbon atom in the presence of a Lewis acid is provided comprising, reacting a material comprising an activated carbon atom with a halogen donor in the presence of a catalytic amount of the Lewis acid; wherein the activated carbon atom is an aromatic carbon atom, a carbon atom alpha to an aromatic ring, or a carbon atom alpha to a silicon atom; and wherein the halogen donor is selected from the group consisting of N-bromosuccinimide, N-iodosuccinimide, N-chlorosuccinimide and N-fluorobenzene-sulfonimide. In some aspects the Lewis acid comprises a metal selected from the group consisting of Zr, Fe, and Al, preferably Zr. Preferably the Lewis acid is $ZrCl_4$. The catalytic amount of the Lewis acid is from about 0.5 mole % to about 25 mole % of the material comprising the activated carbon atom, preferably, $ZrCl_4$ is from about 0.5 mole to about 25 mole % of the material comprising the activated carbon atom.

In some aspects of the method of halogenating, the material is an aromatic compound represented by formula I:

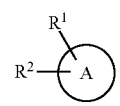

I wherein Ring A is aryl; $R^1$ is selected from the group consisting of —$OR^3$, —$NR^3R^4$, and —$SR^3$; wherein $R^3$ and $R^4$ are each independently selected from the group consisting of hydrogen, $C_{1-8}$ alkyl, $C_{1-8}$ heteroalkyl, $C_{2-8}$ alkenyl, $C_{2-8}$ alkynyl, $C_{6-10}$ aryl, 5- to 10-membered heteroaryl, and 3- to 10-membered heterocycle; $R^3$ and $R^4$ may together with the atom(s) to which they are attached, form a 5-, 6-, or 7-membered cycloalkyl or heterocyclyl; $R^2$ represents 0 to 5 substituents each independently selected from the group consisting of hydrogen, —$OR^3$, —$NR^3R^4$, —$SR^3$, $C_{1-8}$ alkyl, $C_{1-8}$ heteroalkyl, $C_{1-8}$ haloalkyl, $C_{2-8}$ alkenyl, $C_{2-8}$ alkynyl, 3- to 10-membered heterocyclyl, $C_{6-10}$ aryl, and 5- to 10-membered heteroaryl. In some aspects $R^1$ is —$OR^3$, in others $R^1$ is —$NR^3R^4$.

In other aspects of the method of halogenating, the material is an aromatic compound represented by formula III:

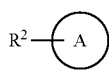

III wherein Ring A is heteroaryl; and $R^2$ represents 0 to 5 substituents each independently selected from the group consisting of hydrogen, $C_{1-8}$ alkyl, $C_{1-8}$ heteroalkyl, $C_{1-8}$ haloalkyl, $C_{2-8}$ alkenyl, $C_{2-8}$ alkynyl, 3- to 10-membered heterocyclyl, $C_{6-10}$ aryl, and 5- to 10-membered heteroaryl.

The aromatic compound may represented by formula IIIa:

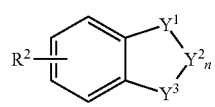

IIIa wherein $R^2$ represents 0 to 4 substituents each independently selected from the group consisting of hydrogen, halogen, $C_{1-8}$ alkyl, $C_{1-8}$ heteroalkyl, $C_{1-8}$ haloalkyl, $C_{2-8}$ alkenyl, $C_{2-8}$ alkynyl, 3- to 10-membered heterocyclyl, $C_{6-10}$ aryl, and 5- to 10-membered heteroaryl; $Y^1$ is selected from the group consisting of —$NR^3$—, —O—, and —S—; each $Y^2$ is independently —$CR^3R^4$—; $Y^3$ is selected from the group consisting of —$NR^3$—, —O—, —$CR^3R^4$— and —S—; wherein $R^3$ and $R^4$ are each independently selected from the group consisting of hydrogen, $C_{1-8}$ alkyl, $C_{1-8}$ heteroalkyl, $C_{2-8}$ alkenyl, $C_{2-8}$ alkynyl, $C_{6-10}$ aryl, 5- to 10-membered heteroaryl, and 3- to 10-membered heterocycle; $R^3$ and $R^4$ may together with the atom(s) to which they are attached, form a 5-, 6-, or 7-membered cycloalkyl or heterocyclyl; and n is 1, 2 or 3. In some aspects, $Y^1$ is —O—.

The aromatic compound may represented by formula IIIb:

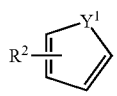

IIIb wherein $Y^1$ is selected from the group consisting of —$NR^3$—, —O—, and —S—. In some aspects $Y^1$ is —$NR^3$.

In other aspects of the method of halogenating, the activated carbon atom is alpha to an aromatic ring and the material is represented by formula V:

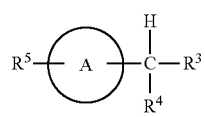

V wherein Ring A is aryl; $R^3$ and $R^4$ are each independently selected from the group consisting of hydrogen, $C_{1-8}$ alkyl, $C_{1-8}$ heteroalkyl, $C_{2-8}$ alkenyl, $C_{2-8}$ alkynyl, $C_{6-10}$ aryl, 5- to 10-membered heteroaryl, and 3- to 10-membered heterocycle; $R^3$ and $R^4$ may together with the atom(s) to which they are attached, form a 5-, 6-, or 7-membered cycloalkyl or heterocyclyl; and $R^5$ represents 0 to 5 substituents each independently selected from the group consisting of hydrogen and halogen.

In yet other aspects of the method of halogenating, the material is elemental carbon comprising an aromatic carbon compound. The elemental carbon comprising an aromatic carbon compound may be graphite or charcoal.

In still other aspects of the method of halogenating wherein the activated carbon atom is alpha to silicon and the material is represented by formula VIIa:

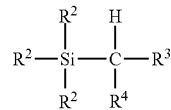

VIIa wherein $R^2$ is independently selected from the group consisting of hydrogen, —$OR^3$, —$NR^3R^4$, —$SR^3$, $C_{1-8}$ alkyl, $C_{1-8}$ heteroalkyl, $C_{1-8}$ haloalkyl, $C_{2-8}$ alkenyl, $C_{2-8}$ alkynyl, 3- to 10-membered heterocyclyl, $C_{6-10}$ aryl, and 5- to 10-membered heteroaryl; and $R^3$ and $R^4$ are each independently selected from the group consisting of hydrogen, $C_{1-8}$ alkyl, $C_{1-8}$ heteroalkyl, $C_{2-8}$ alkenyl, $C_{2-8}$ alkynyl, $C_{6-10}$ aryl, 5- to 10-membered heteroaryl, and 3- to 10-membered heterocycle.

In another embodiment, the method of halogenating an activated carbon atom in the presence of a Lewis acid comprises reacting a material comprising an activated carbon atom with a halogen donor in the presence of a catalytic amount of the Lewis acid; wherein the Lewis acid comprises a metal selected from the group consisting of Zr, Fe and Al; wherein the activated carbon atom is an aromatic carbon atom, a carbon atom alpha to an aromatic ring, or a carbon atom alpha to a silicon atom; and wherein the reacting is done in the presence of light. Preferably the metal is Zr, more preferably $ZrCl_4$. The light may be incandescent or laser light, preferably laser light.

EXAMPLES

The following examples are offered to illustrate, but not to limit, the claimed invention.

Bromination using NBS has been found to be applicable for use with a wide range of aromatic starting materials or substrates, as is summarized in Table 1. For example, anisole can be brominated by use of 1 equivalent of NBS in the presence of 5 mol % of $ZrCl_4$ at −78° C. to afford p-bromoanisole in 98% yield as sole product (Table 1, Entry 1). However, in the absence of $ZrCl_4$ the halogenation does not proceed, even at room temperature (Table 1, Entry 1).

All of the substrates shown in Table 1 were brominated to give the corresponding monobromo products in excellent yield and regioselectivity. In most cases, the reaction can proceed at very low temperature and no further purification is necessary. In addition, Table 1 reveals that the halogenation of the present invention is compatible with a variety of substituents.

TABLE 1

$ZrCl_4$ Catalyzed Bromination of Aromatic Compounds

| Entry | Starting Material | Temp (° C.) | Time (h) | Conversion (%)[b] | Product (II)[d] |
|---|---|---|---|---|---|
| 1[a] | OMe (phenyl) | −78<br>r.t.<br>r.t.[c] | 5<br>1<br>12[c] | 98<br>96<br><1[c] | OMe-C6H4-Br |

TABLE 1-continued

ZrCl₄ Catalyzed Bromination of Aromatic Compounds

| Entry | Starting Material | Temp (° C.) | Time (h) | Conversion (%)[b] | Product (II)[d] |
|---|---|---|---|---|---|
| 2[a] | 2-methoxynaphthalene | −78<br>r.t. | 2<br>2 | >99<br>>99 | 1-bromo-2-methoxynaphthalene |
| 3[a] | 1-methoxynaphthalene | −78<br>0<br>r.t. | 1.5<br>2<br>2 | 81<br>91<br>95 | 4-bromo-1-methoxynaphthalene |
| 4[a] | 1-aminonaphthalene | −78 | 1.5 | 93 | 4-bromo-1-aminonaphthalene |
| 5[a] | pyrrole | 0<br>r.t. | 4<br>4 | >99<br>>99 | 2-bromopyrrole |
| 6[a] | 2-naphthol | −78<br>0<br>r.t. | 3<br>2<br>2 | >99<br>>99<br>>99 | 1-bromo-2-naphthol |
| 7[a] | 2,3-dihydrobenzofuran | r.t. | 1 | >99 | 5-bromo-2,3-dihydrobenzofuran |

[a]Reaction conditions: Substrate (0.5 mmol), NBS (0.5 mmol), ZrCl₄ (5 mol %), CH₂Cl₂ (4 mL).
[b]Determined by ¹H NMR.
[c]In the absence of ZrCl₄.
[d]See spectroscopic data for characterization.

Chlorination using NCS has been found to be applicable for use with a wide range of aromatic starting materials or substrates, as is shown in Table 2. All the substrates treated with 1 equivalent of NCS and 5 mole % of $ZrCl_4$ afforded the corresponding chlorinated compounds. The reaction at room temperature afforded a high yield of chlorinated product with high regioselectivity. In some cases, a small amount of regioisomers (Entry 3) or dichlorinated products (Entries 4 and 5) were observed.

TABLE 2

$ZrCl_4$ Catalyzed Chlorination of Aromatic Compounds by NCS

| Entry | Starting Material | Temp (°C.) | Time (h) | Conversion (%)[b] | Product (II)[c] |
|---|---|---|---|---|---|
| 1[a] | phenyl methyl ether (OMe) | r.t. | 12 | 92 | 4-chloroanisole |
| 2[a] | 2-methoxynaphthalene | r.t. | 12 | 97 | 1-chloro-2-methoxynaphthalene |
| 3[a] | 1-methoxynaphthalene | r.t. | 12 | 94 | 1-methoxy-chloronaphthalene, 2-Cl:4-Cl (13:87)[b] |
| 4[a] | pyrrole | r.t. | 6 | 92 | chloropyrrole, 1-Cl:1,4-di-Cl (83:17)[b] |
| 5[a] | 1-naphthol | 0 | 6 | 83 | chloro-1-naphthol, 4-Cl:2,4-di-Cl (75:25)[b] |
| 6[a] | 2-naphthol | 0 / r.t. | 6 / 6 | >99 / >99 | 1-chloro-2-naphthol |
| 7[a] | 2,3-dihydrobenzofuran | r.t. | 12 | 92 | chloro-2,3-dihydrobenzofuran |

[a]Reaction conditions: Substrate (0.5 mmol), NCS (0.5 mmol), $ZrCl_4$ (5 mol %), $CH_2Cl_2$ (4 mL).
[b]Determined by $^1H$ NMR.
[c]See spectroscopic data for characterization.

Iodination using NIS has been found to be applicable for use with a wide range of aromatic starting materials or substrates. As shown in Table 3, the iodination provides good yields and regioselectivities. In Entry 2, trace di-iodinated products were observed.

TABLE 3

ZrCl$_4$ Catalyzed Iodination of Aromatic Compounds by NIS

| Entry | Starting Material | Temp (°C.) | Time (h) | Conversion (%)[b] | Product (II)[c] |
|---|---|---|---|---|---|
| 1[a] | OMe-phenyl | r.t. | 12 | 95 | 4-iodoanisole |
| 2[a] | aniline (NH$_2$) | 0 | 2 | >99 | iodoaniline; 4-I:2,4-di-I (99:1)[b] |
| 3[a] | 2-methoxynaphthalene | 0 | 6 | 96 | 1-iodo-2-methoxynaphthalene |
| 4[a] | 1-methoxynaphthalene | −78 / 0 / r.t. | 6 / 6 / 6 | 93 / >99 / >99 | 4-iodo-1-methoxynaphthalene |
| 5[a] | 1-aminonaphthalene | −78 | 6 | 65 | iodo-1-aminonaphthalene; 4-I:2,4-di-I (36:64)[b] |
| 6[a] | 2-naphthol | −78 / 0 / r.t. | 3 / 2 / 2 | >99 / >99 / >99 | 1-iodo-2-naphthol |

[a]Reaction conditions: Substrate (0.5 mmol), NIS (0.5 mmol), ZrCl$_4$ (5 mol %), CH$_2$Cl$_2$ (4 mL).
[b]Determined by $^1$H NMR.
[c]See spectroscopic data for characterization.

Fluorination using NFSI has been found to be applicable for use with a wide range of aromatic starting materials or substrates, as is illustrated in Table 4. Fluorination is one of the most difficult operations in organic synthesis. A mild fluorinating reagent, NFSI was selected as the fluorine source. The reactions of 1-methoxylnaphthalene, 2-methoxylnaphthalene, and pyrrole with NFSI catalyzed by ZrCl$_4$ gave the corresponding fluorinated products (Table 4, Entries 1, 2, and 3 respectively). As shown in Entry 1, increasing the amount of catalyst increased the yield of the fluorinated product.

TABLE 4

ZrCl₄ Catalyzed Fluorination of Aromatic Compounds by NFSI

| Entry | Starting Material | Temp (° C.) | Time (h) | Conversion (%)[b] | Product (II)[f] |
|---|---|---|---|---|---|
| 1[a] | 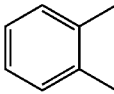 | r.t.<br>r.t.<br>r.t. | 6<br>6<br>6 | 70[c]<br>43[d]<br>28[e] | 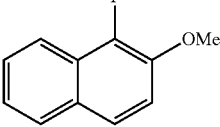 |
| 2[a] | 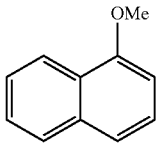 [SMILES: COc1cccc2ccccc12] | r.t. | 12 | 31[e] | 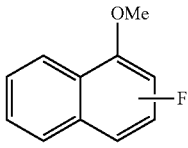<br>2-F:4-F<br>(43:57)[b] |
| 3[a] |  | r.t. | 12 | 53[e] | 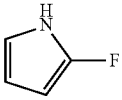 |

[a]Reaction conditions: Substrate (0.5 mmol), NFSI (0.5 mmol), ZrCl₄ (5 mol %), CH₂Cl₂ (4 mL).
[b]Determined by ¹H NMR.
[c]With 1 equiv. of ZrCl₄.
[d]With 50 mol % of ZrCl₄.
[e]With 20 mol % of ZrCl₄.
[f]See spectroscopic data for characterization.

The reaction of NBS and toluene in the presence of 5 mole % ZrCl₄ did not give the ring substituted product, but rather benzyl bromide almost exclusively. Table 5 shows some additional examples. The reaction also proceeds smoothly in the presence of FeCl₃ or AlCl₃ with almost the same reactivity as that of ZrCl₄. Without wishing to be bound by any theory of interpretation, it is believed that this reaction may proceed by a radical mechanism. In fact, the reaction does not proceed at all in the presence of a radical inhibitor.

TABLE 5

ZrCl₄ Catalyzed Radical Bromination of Aromatic Compound by NBS[a]

| Entry | Starting Material | Temp (° C.) | Time (h) | Conversion (%)[b] | Product (II)[c] |
|---|---|---|---|---|---|
| 1 | 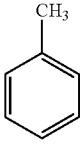 | r.t. | 24 | 89 | 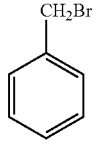 |
| 2 | 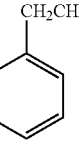 | 0 | 6 | >99 | 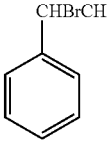 |
| 3 | 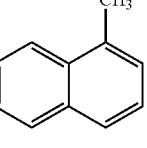 | 0<br>r.t. | 5<br>2 | 85<br>88 | 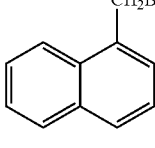 |
| 4 | 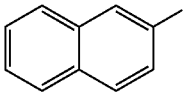 | 0<br>r.t. | 5<br>2 | 80<br>91 | 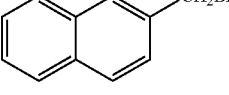 |

TABLE 5-continued

ZrCl₄ Catalyzed Radical Bromination of Aromatic Compound by NBS[a]

| Entry | Starting Material | Temp (°C.) | Time (h) | Conversion (%)[b] | Product (II)[c] |
|---|---|---|---|---|---|
| 5 | 2-bromotoluene | 0 | 6 | 94 | 2-bromobenzyl bromide |
| 6 | 3,4-dichlorotoluene | 0 | 6 | 89 | 3,4-dichlorobenzyl bromide |
| 7 | 3,4-difluorotoluene | 0 | 6 | 91 | 3,4-difluorobenzyl bromide |

[a]Reaction conditions: Substrate (0.5 mmol), NCS (0.5 mmol), ZrCl₄ (5 mol %), CH₂Cl₂ (4 mL).
[b]Determined by ¹H NMR.
[c]See spectroscopic data for characterization.

Toluene can be dibrominated and tribrominated in the presence of an excess amount of NBS. For example, as shown in Scheme 19, dibrominated toluene can be obtained as the major product using 6 equivalents of NBS, AlCl₃ (5 mole %), in CH₂Cl₂ at room temperature for 22 hours. As shown in Scheme 20, tribrominated toluene can be obtained as the major product using 10 equivalents of NBS, ZrCl₄ (5 mole %), in CH₂Cl₂ at reflux for 22 hours.

Scheme 19

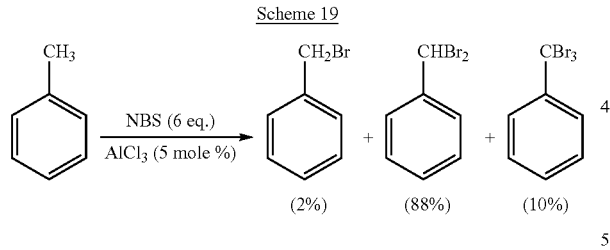

Scheme 20

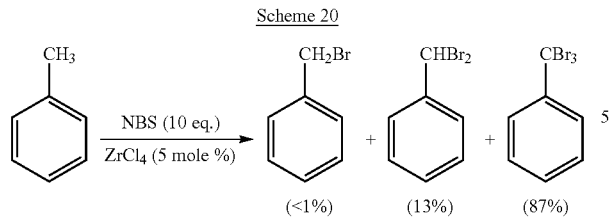

Other halogenating agents were also studied including, for example 1,3-dihalo-5,5-dimethylhydantoins. As shown in Table 6, the bromination of toluene using 1,3-dibromo-5,5-dimethylhydantoin was studied with various acids. The reactions were run by adding to a suspension of the acid (0.05 mmol) in dichloromethane (2 mL), a solution of toluene (0.5 mmol) and 1,3-dibromo-5,5-dimethylhydantoin (0.25 mmol) in dichloromethane (2 mL) at room temperature. The mixture was stirred for 2 h at room temperature under room light. The reaction was quenched with saturated aqueous NaHCO₃ solution and extracted with diethyl ether. The organic layer was subjected to GC analysis using 1,2-dichlorobenzene as a internal standard.

TABLE 6

Acid Catalyzed Bromination of Toluene[a]

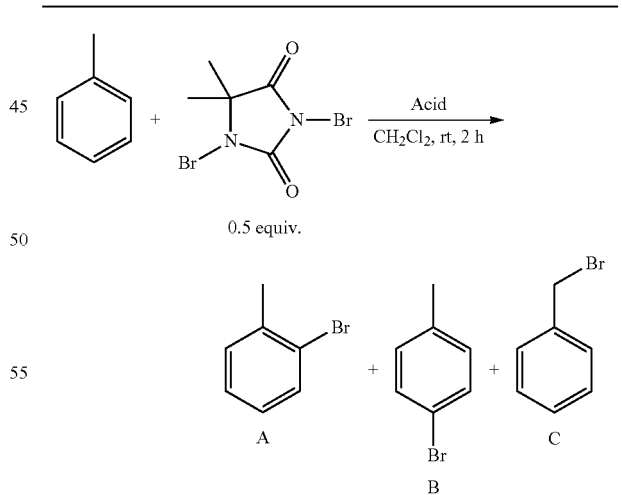

| | | % Yield[c] | | |
|---|---|---|---|---|
| Entry | Acid (mol %)[b] | A | B | C |
| 1 | none | 0 | 0 | 0 |
| 2[d] | ZrCl₄ (10) | 0 | 0 | 39 |

TABLE 6-continued

| | | | | |
|---|---|---|---|---|
| 3 | ZrCl₄ (10) | 0 | 0 | 86 |
| 4 | Zr(OiPr)₄·H₂O (10) | 0 | 0 | 32 |
| 5 | TiCl₄ (10) | 2 | 2 | 71 |
| 6 | AlCl₃ (10) | 5 | 4 | 70 |
| 7 | Tf₂NAlCl₂ (10) | 1 | 1 | 76 |
| 8 | Cy₂BCl (10) | 0 | 0 | 71 |
| 9 | TfOH (50) | 49 | 45 | 0 |
| 10 | Tf₂NH (50) | 48 | 46 | 0 |
| 11 | (C₄F₉SO₂)₂NH (50) | 44 | 42 | 0 |

[a] Reactions were carried out in dichloromethane at room temperature for 2 hours with 0.5 equivalent of 1,3-dibromo-5,5-dimethylimidazolidine-2,4-dione under room light unless otherwise noted.
[b] Cy = cyclohexyl, Tf = trifluoromethanesulfonyl.
[c] Yields were determined by GC analysis.
[d] 1.0 equivalent of NBS was used instead of 1,3-dibromo-5,5-dimethylimidazolidine-2,4-dione.

The halogenation of other substrates with 1,3-dihalo-5,5-dimethylhydantoins was studied as shown in Table 7.

TABLE 7

Acid Catalyzed Halogenation of Aromatic compounds[a]

| Entry | Starting Material | Acid (mol %) | Time (h) | Yield (%) | Product (II)[c] |
|---|---|---|---|---|---|
| 1 | PhCH₂CH₃ | ZrCl₄ (10) | 2 | 98[b] | PhCHBrCH₃ |
| 2[c] | PhCH₂CH₃ | ZrCl₄ (10) | 24 | 76[b] | PhCHClCH₃ |
| 3 | PhCH₂CH₃ | Tf₂NH (50) | 4 | 93[b] o/p = 1/1/3 | Br-C₆H₄-CH₂CH₃ |
| 4 | o-Br-C₆H₄-Me | ZrCl₄ (10) | 6 | 89[d] | 4-Br-C₆H₄-CH₂Br |
| 5 | o-Br-C₆H₄-Me | Tf₂NH (50) | 10 | 45[d] | 2,4-Br₂-C₆H₃-Me |
| 6 | o-MeO-C₆H₄-Me | ZrCl₄ (10) | 1 | 99[b] | 2-OMe-4-Br-C₆H₃-Me |
| 7 | o-MeO-C₆H₄-Me | Tf₂NH (50) | 1.5 | 95[b] | 2-OMe-4-Br-C₆H₃-Me |

[a] Reactions were carried out in dichloromethane at room temperature with 0.5 equivalent of 1,3-dibromo-5,5-dimethylimidazolidine-2,4-dione unless otherwise noted.
[b] Yields were determined by NMR.
[c] 0.5 equivalent of 1,3-dichloro-5,5-dimethylimidazolidine-2,4-dione was used instead of 1,3-dibromo-5,5-dimethylimidazolidine-2,4-dione.
[d] Isolated yield.

The bromination reaction is accelerated in the presence of light. For example, as shown in Table 8, toluene can be brominated using 0.5 equivalents of 1,3-dibromo-5,5-dimethylimidazolidine-2,4-dione, ZrCl$_4$ (10 mole %), in CH$_2$Cl$_2$ at room temperature for 2 hours. When the reaction is run under standard indoor lighting, a 95% yield of product A is obtained. When the reaction vessel covered in aluminum foil to block light, less than 1% yield of A is obtained.

TABLE 8

Bromination Rate of Toluene Accelerated in Presence of Light

| | | % Yield | | |
|---|---|---|---|---|
| Entry | Light Conditions | A | B | C |
| 1 | room light | 94 | 0 | 0 |
| 2 | in dark[a] | <1 | 5 | 9 |

[a]Reaction vessel was covered with aluminum foil.

Laser light can also be used to accelerate bromination. For example, as shown in Table 9, ethylbenzene can be brominated using 0.5 equivalents of 1,3-dibromo-5,5-dimethylimidazolidine-2,4-dione, ZrCl$_4$ (10 mole %), in CH$_2$Cl$_2$ at room temperature for 2 hours. When the reaction is run under standard indoor lighting, a 98% yield of the alpha brominated product is obtained. When the reaction vessel covered in aluminum foil to block light, less than 1% of the alpha brominated product is obtained. At −78° C. under standard indoor lighting, less than 1% of the alpha brominated product is obtained. When a green laser (Wavelength 532 nm, Max output power <5 mW) is shined on the reaction at −78° C., a 63% yield of the alpha brominated product is obtained.

TABLE 9

Bromination Rate of Ethylbenzene Accelerated in Presence of Light

| Entry | Light Conditions | Temp (° C.) | Yield (%) |
|---|---|---|---|
| 1 | room light | rt | 98 |
| 2 | in dark[a] | rt | <1 |
| 3 | room light | −78 °C. | <1 |
| 4 | green laser[b] | −78 °C. | 63 |

[a]Reaction vessel was covered with aluminum foil.
[b]Wavelength 532 nm, Max output power <5 mW.

Silane compounds can be monobrominated, dibrominated and tribrominated in the presence of an excess amount of NBS and a Lewis acid catalyst such as AlCl$_3$, FeCl$_3$ or ZrCl$_4$. For example, as shown in Scheme 21, (bromomethyl)trimethylsilane can be obtained as the major product in 32% isolated yield using NBS, AlCl$_3$ (5 mole %), in CH$_2$Cl$_2$ at room temperature for 18 hours. As shown in Scheme 22, (1,1-dibromoethyl)triethylsilane can be obtained as the major product in 54% isolated yield using NBS, ZrCl$_4$ (5 mole %), in CH$_2$Cl$_2$ at room temperature for 18 hours. The major products were isolated by distillation.

Alternatively, tetramethylsilane can be brominated according to Scheme 21 using 1,3-dibromo-5,5-dimethylimidazolidine-2,4-dione. Tetramethylsilane (4 mmol) and 1,3-dibromo-5,5-dimethylimidazolidine-2,4-dione (1 mmol) was added to a suspension of ZrCl$_4$ (0.1 mmol) in dichloromethane (4 mL) at room temperature. The mixture was stirred for 36 h at room temperature under room light. A yield of bromomethyltrimethylsilane was determined by $^1$H NMR analysis of the reaction mixture to be 70% (1.4 mmol, based on ½ of 1,3-dibromo-5,5-dimethylimidazolidine-2,4-dione).

Scheme 21

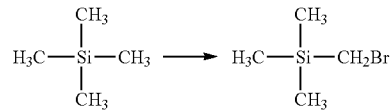

Scheme 22

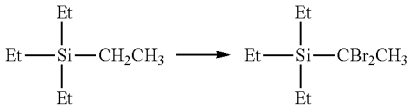

Figure 2:
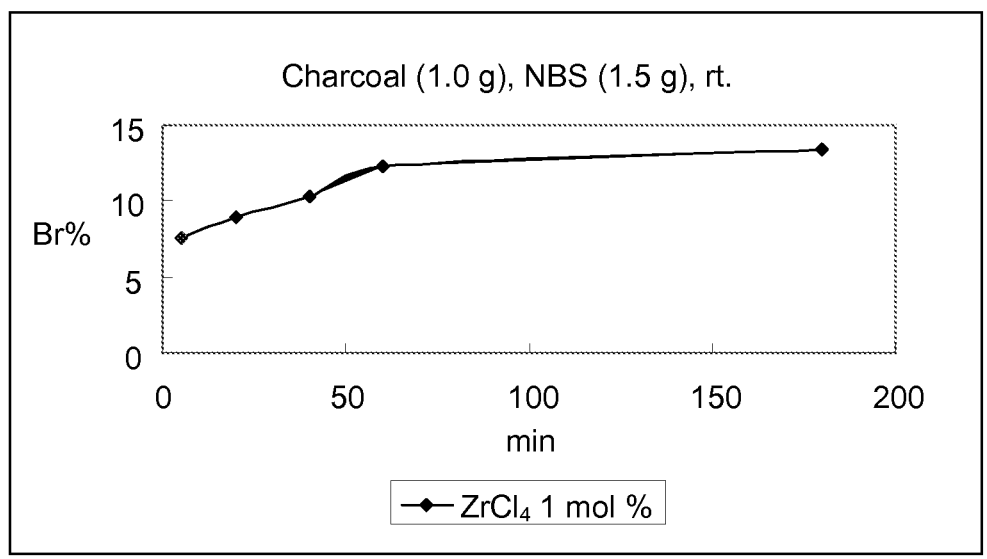
FIG. 2 is a graph depicting the bromination of charcoal.

Elemental carbon comprising aromatic rings can be halogenated using the methods of the present invention. For example, FIG. 1 illustrates the bromination of 1.0 g of graphite using 0.5 g of N-bromosuccinimide and 0.8 mol % ZrCl$_4$ at rt in CH$_2$Cl$_2$. FIG. 2 illustrates the bromination of 1.0 g of charcoal using 0.5 g of N-bromosuccinimide and 0.8 mol % ZrCl$_4$ at rt in CH$_2$Cl$_2$. In both cases, bromination reaction is fast, and nearly complete within the first hour. The weight % bromide in the product is determined by elemental analysis.

The catalyst loading can be as low as 0.1%, but higher catalyst loading exhibits higher reactivity for graphite. Catalyst loadings of 1 and 3 mole % have been found to be effective. FeCl$_3$ and AlCl$_3$ can also work as efficient Lewis acid catalyst in this reaction and gave similar results. Under the same reaction conditions, but without catalyst, the bromination procedure is very slow, only 0.1% Br was detected even after 24 h. Furthermore, the chlorination by N-chlorosuccinimide (NCS) and the iodination by N-iodosuccinimide (NIS) of charcoal or graphite proceed well under the same reaction conditions and give corresponding halogenated carbon products.

The halogenated elemental carbon comprising aromatic rings can be further functionalized. Metal-catalyzed cross coupling reactions are known to one skilled in the art. Aryl halides and heteroaryl halides can either be used directly in such reactions or converted to an aryl or heteroaryl metal compound for use in such reactions. Brominated graphite prepared according to the methods of the present invention was coupled to pyridine-3-boronic acid using Suzuki-Miyaura coupling reaction conditions (G. Lu, R. Franzen, Q. Zhang, Y. Xu, *Tetrahedron Lett.* 46, 4255 (2005); T. Tagata, M. Nishida, *J. Org. Chem.* 68, 9412 (2003)) forming pyridyl functionalized graphite which can act as a ligand for metals. Thus, the pyridyl functionalized graphite was treated with Pd(OAc)$_2$ to form Pd catalyst (XI) as shown in Scheme 23.

Scheme 23

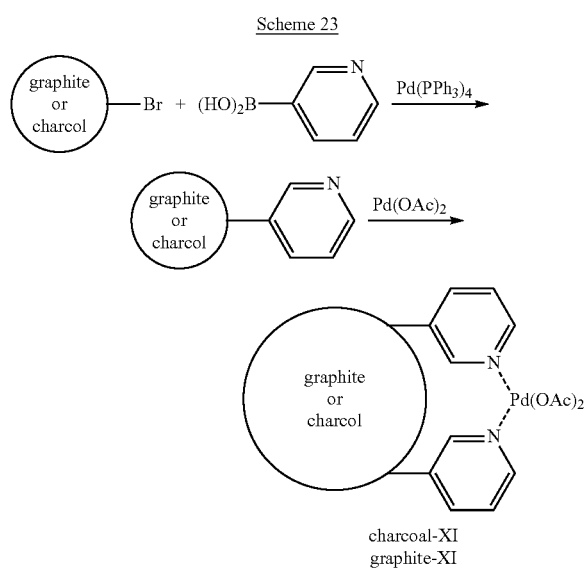

In a similar manner, brominated graphite was coupled (pyridin-2-yl)pyridin-4-yl-4-boronic acid using Suzuki-Miyaura coupling reaction conditions forming a bipyridyl functionalized graphite which can act as a ligand for metals. Thus, the bipyridyl functionalized graphite was treated with Pd(OAc)$_2$ to form Pd catalyst (XII) as shown in Scheme 24.

Scheme 24

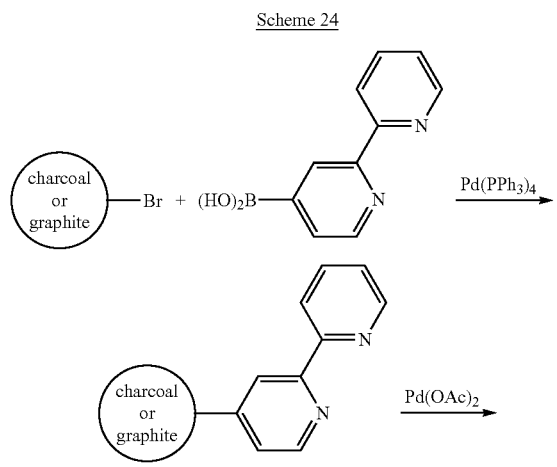

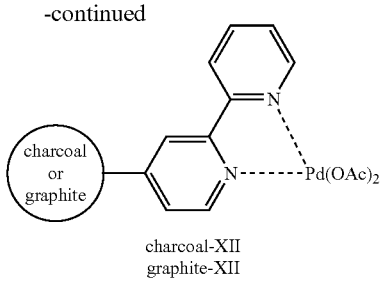

charcoal-XII
graphite-XII

Each of the Pd catalysts obtained was applied in the air oxidation of 1-phenylethanol and the results are summarized in Table 10. The pyridyl functionalized charcoal and graphite ligands are more efficient ligands than corresponding simple pyridine (23% yield) and bipyridine (<6% yield) ligands, respectively. The activity of graphite functionalized catalyst is much higher than charcoal functionalized catalyst, with the pyridyl functionalized graphite catalyst affording the highest yields. A similar reaction run with non-functionalized charcoal or graphite and Pd(OAc)$_2$ does not work on this reaction at all, supporting the idea that the functionalized graphite or charcoal ligand in combination with the Pd catalyst, increases the reactivity of the Pd catalyst.

TABLE 10

Air oxidation of 1-phenylethanol.

| Entry | Catalyst | Time (h) | Yield (%)[c] |
|---|---|---|---|
| 1 | charcoal-XI[a] | 72 | 56.7 |
| 2 | charcoal-XII[a] | 88 | 20.2 |
| 3 | graphite-XI[b] | 72 | 100 |
| 4 | graphite-XII[b] | 88 | 30.2 |

[a]0.2 mol % loading.
[b]0.3 mol % loading.
[c]Determined by $^1$H NMR.

The application of the pyridyl functionalized graphite Pd catalyst (graphite-XI) to the air oxidation of alcohols was further extended to other alcohols as shown in Table 11. The oxidized products were isolated by filtration and concentration of the filtrate. The results show that the catalyst is generally applicable to a wide range of alcohols, and gives the corresponding products in good yields. The mild reaction conditions are easily and safely handled. The stable, easily removable and reusable characteristics of the catalysts are great advantages in industrial processes.

TABLE 11

Air oxidation of various alcohols.

| Entry | Alcohol | Time (h) | Yield (%) |
|---|---|---|---|
| 1 | 1-phenylethanol | 48 | 95.7 |
| 2 | 2-octanol | 96 | 69.5 |
| 3 | benzyl alcohol | 48 | 84.7 |
| 4 | 2-heptanol | 72 | 64.8 |
| 5 | 4-isopropylbenzyl alcohol | 48 | 81.8 |
| 6 | trans-2-methylcyclohexanol | 72 | 53.4 |
| 7 | 3-octanol | 96 | 55.4 |
| 8 | 3,3-dimethyl-2-butanol | 96 | 71.8 |
| 9 | 2-hexanol | 96 | 65.8 |
| 10 | 1-(4-methylphenyl)ethanol | 48 | 73.6 |

EXPERIMENTAL

All reagents unless otherwise indicated were commercially available from Aldrich, Boron Molecular Inc or Strem. All reactions were carried out in oven-dried glassware with magnetic stirring under nitrogen atmosphere unless otherwise noted. Zirconium(IV) chloride, aluminum(III) chloride and bistrifluoromethanesulfonimide were handled in a glove box. A green laser pointer (Wavelength 532 nm, Max output power <5 mW) was purchased from Leadlight Technology, Inc. $^1$H NMR spectra were recorded on a Bruker Avance 400 (400 MHz) or 500 (500 MHz) spectrometer at ambient temperature. Chemical shift values (δ) are expressed in ppm downfield relative to internal standard (tetramethylsilane at 0 ppm). Multiplicities are indicated as s (singlet), d (doublet), t (triplet), q (quartet), m (multiplet) and br (broad). Elemental analysis was performed by Midwest Microlab, LLC, Indianapolis, Ind., USA. Analytical thin layer chromatography (TLC) was performed on E. Merck precoated TLC plates (silica gel 60 GF254, 0.25 mm). Visualization was accomplished with UV light and phosphomolybdic acid solution in ethanol by heating. All solvents were freshly distilled. All other reagents and starting materials, unless otherwise noted, were purchased from commercial vendors and used without further purification. Charcoal was purchased from Sigma-Aldrich company (St. Louis, Mo., USA): Activated carbon, Darco®, 12-20 mesh, granular, catalog #242241-250G. Graphite was purchased from Sigma-Aldrich company (St. Louis, Mo., USA), Graphite, powder, −325 mesh, >99.99%, catalog #496596-113.4G.

Example 1

General Procedure for the Halogenation of Aromatic Compounds

To a solution of NXS (X=Br, Cl, I) or NFSI (0.5 mmol) in CH$_2$Cl$_2$ (4.0 mL) under a nitrogen atmosphere and cooled to the desired temperature is added ZrCl$_4$ (0.025 mmol), followed by the substrate (0.5 mmol) under nitrogen atmosphere. The reaction was stirred until completion and then quenched by saturated NaHCO$_3$ aqueous solution (4 mL). The aqueous layer was extracted with CH$_2$Cl$_2$ (3×4 mL), and the combined organic phases were washed with brine (4 mL) and dried over Na$_2$SO$_4$ to give the desired product. The structure of the product may be determined by comparison of $^1$H NMR and $^{13}$C NMR with reported data, or by other analytical techniques known to one skilled in the art.

Example 2

1-Halo-4-methoxy-benzene

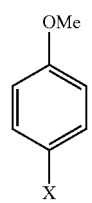

(X=Cl): $^1$H NMR (500 MHz, CDCl$_3$) δ 7.23 (m, 2H), 6.82 (m, 2H), 3.77 (s, 3H). (X=Br): $^1$H NMR (500 MHz, CDCl$_3$) δ 7.37 (m, 2H), 6.78 (m, 2H), 3.77 (s, 3H). (X=I): $^1$H NMR (500 MHz, CDCl$_3$) δ 7.54 (m, 2H), 6.68 (m, 2H), 3.77 (s, 3H).

Example 3

1-Halo-2-methoxy-naphthalene

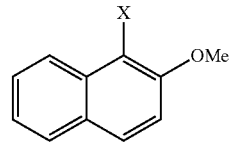

(X=F): $^1$H NMR (400 MHz, CDCl$_3$) δ 8.00 (d, 1H, J=8.5 Hz), 7.68 (m, 2H), 7.54 (m, 1H), 7.35 (m, 1H), 7.24 (m, 1H), 3.95 (s, 3H). (X=Cl): $^1$H NMR (500 MHz, CDCl$_3$) δ 8.21 (d, 1H, J=8.5 Hz), 7.76 (m, 2H), 7.55 (m, 1H), 7.38 (m, 1H), 7.26 (d, 1H, J=9.0 Hz), 4.00 (s, 3H). (X=Br): $^1$H NMR (400 MHz, CDCl$_3$) δ 8.20 (dd, 1H, J=0.8, 8.5 Hz), 7.75 (m, 2H), 7.54 (m, 1H), 7.36 (m, 1H), 7.20 (d, 1H, J=9.0 Hz), 3.97 (s, 3H). (X=I): $^1$H NMR (400 MHz, CDCl$_3$) δ 8.11 (d, 1H, J=8.6 Hz), 7.74 (d, 1H, J=8.9 Hz), 7.68 (d, 1H, J=8.0 Hz), 7.50 (m, 1H), 7.34 (m, 1H), 7.11 (d, 1H, J=9.0 Hz), 3.95 (s, 3H).

Example 4

1-Halo-4-methoxy-naphthalene

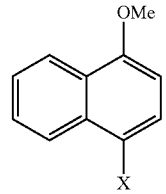

(X=F): $^1$H NMR (400 MHz, CDCl$_3$) δ 8.30-7.50 (m, 4H), 6.99 (m, 1H), 6.59 (m, 1H), 3.91 (s, 3H). (X=Cl): $^1$H NMR (400 MHz, CDCl$_3$) δ 8.26 (d, 1H, J=8.0 Hz), 8.17 (d, 1H, J=8.4 Hz), 7.58 (m, 1H), 7.50 (m, 2H), 6.65 (d, 1H, J=8.2 Hz), 3.93 (s, 3H). (X=Br): $^1$H NMR (500 MHz, CDCl$_3$) δ 8.25 (d, 1H, J=8.0 Hz), 8.14 (d, 1H, J=8.5 Hz), 7.62 (d, 1H, J=8.5 Hz), 7.58 (t, 1H, J=7.5 Hz), 7.50 (t, 1H, J=7.5 Hz), 6.62 (d, 1H, J=8.5 Hz), 3.93 (s, 3H). (X=I): $^1$H NMR (400 MHz, CDCl$_3$) δ 8.19 (dd, 1H, J=0.7, 8.4 Hz), 7.98 (d, 1H, J=8.4 Hz), 7.88 (d, 1H, J=8.2 Hz), 7.54 (m, 1H), 7.46 (m, 1H), 6.49 (d, 1H, J=8.2 Hz), 3.90 (s, 3H).

Example 5

2-Halo-1-methoxy-naphthalene

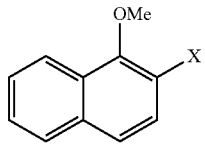

(X=F): $^1$H NMR (400 MHz, CDCl$_3$) δ 8.20-7.20 (m, 6H), 4.08 (d, 3H, J=1.9 Hz). (X=Cl): $^1$H NMR (400 MHz, CDCl$_3$) δ 7.2-8.2 (m, 6H), 3.99 (s, 3H).

Example 6

2-Bromo-naphthalen-1-ylamine

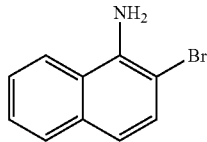 [SMILES: Nc1c(Br)ccc2ccccc12]

$^1$H NMR (500 MHz, CDCl$_3$) δ 7.72 (m, 2H), 7.42 (m, 3H), 7.12 (d, 1H, J=9.0 Hz), 4.56 (br s, 2H).

Example 7

4-Iodo-naphthalen-1-ylamine

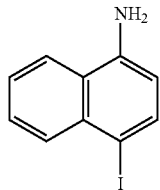 [SMILES: Nc1ccc(I)c2ccccc12]

$^1$H NMR (400 MHz, CDCl$_3$) δ 7.81 (m, 2H), 7.44 (m, 3H), 6.54 (d, 1H, J=7.9 Hz), 4.65 (br s, 2H).

Example 8

2,4-Diiodo-naphthalen-1-ylamine

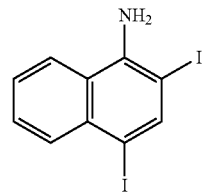 [SMILES: Nc1c(I)cc(I)c2ccccc12]

$^1$H NMR (400 MHz, CDCl$_3$) δ 8.02 (d, 1H, J=7.7 Hz), 7.49 (m, 2H), 7.79 (m, 2H), 4.62 (br s, 2H).

Example 9

2-Halo-1H-pyrrole

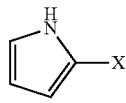

(X=F): $^1$H NMR (400 MHz, CDCl$_3$) δ 6.83 (m, 1H), 6.16 (m, 2H), NH not observed. (X=Cl): $^1$H NMR (400 MHz, CDCl$_3$) δ 8.27 (br s, 1H), 6.64 (m, 1H), 6.15 (m, 1H), 6.04 (m, 1H). (X=Br): $^1$H NMR (400 MHz, CDCl$_3$) δ 8.26 (br s, 1H), 6.77 (m, 1H), 6.25 (m, 1H), 6.22 (m, 1H).

Example 10

2,5-Diiodo-1H-pyrrole

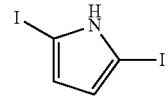

$^1$H NMR (400 MHz, CDCl$_3$) δ 8.29 (br s, 1H), 5.97 (s, 2H).

Example 11

1-Halo-naphthalen-2-ol

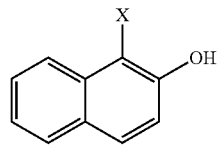

(X=Cl): $^1$H NMR (400 MHz, CDCl$_3$) δ 8.03 (d, 1H, J=8.5 Hz), 7.74 (d, 1H, J=8.2 Hz), 7.65 (d, 1H, J=8.9 Hz), 7.53 (m, 1H), 7.36 (m, 1H), 7.23 (d, 1H, J=8.9 Hz), 6.00 (s, 1H). (X=Br): $^1$H NMR (500 MHz, CDCl$_3$) δ 8.00 (d, 1H, J=8.5 Hz), 7.74 (d, 1H, J=8.0 Hz), 7.70 (d, 1H, J=8.5 Hz), 7.54 (m, 1H), 7.36 (m, 1H), 7.24 (d, 1H, J=9.0 Hz), 5.94 (s, 1H). (X=I): $^1$H NMR (400 MHz, CDCl$_3$) δ 7.92 (d, 1H, J=9.0 Hz), 7.67 (t, 2H, J=8.7 Hz), 7.50 (t, 1H, J=7.4 Hz), 7.33 (t, 1H, J=7.4 Hz), 7.19 (d, 1H, J=9.0 Hz), 6.06 (br s, 1H).

Example 12

5-Chloro-2,3-dihydro-benzofuran

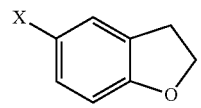

(X=Cl): $^1$H NMR (400 MHz, CDCl$_3$) δ 7.13 (m, 1H), 7.04 (dd, 1H, J=2.3, 8.5 Hz), 6.68 (d, 1H, J=8.5 Hz), 4.56 (t, 2H, J=8.7 Hz), 3.18 (t, 2H, J=8.7 Hz). (X=Br): $^1$H NMR (400 MHz, CDCl$_3$) δ 7.26 (t, 1H, J=0.9 Hz), 7.18 (dd, 1H, J=2.1, 8.4 Hz), 6.64 (d, 1H, J=8.4 Hz), 4.55 (t, 2H, J=8.7 Hz), 3.18 (t, 2H, J=8.7 Hz).

Example 13

4-Chloro-naphthalen-1-ol

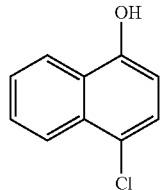 [SMILES: Oc1ccc(Cl)c2ccccc12]

$^1$H NMR (400 MHz, CDCl$_3$) δ 8.15 (m, 2H), 7.53 (m, 2H), 7.30 (d, 1H, J=8.0 Hz), 6.65 (d, 1H, J=8.0 Hz), 5.26 (s, 1H).

Example 14

2,4-Dichloro-naphthalen-1-ol

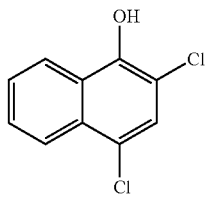 [SMILES: Oc1c(Cl)cc(Cl)c2ccccc12]

$^1$H NMR (400 MHz, CDCl$_3$) δ 8.20 (m, 2H), 7.60 (m, 2H), 7.31 (s, 1H), 5.95 (s, 1H).

Example 15

4-Iodo-phenylamine

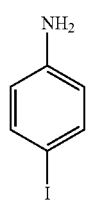

$^1$H NMR (400 MHz, CDCl$_3$) δ 7.38 (m, 2H), 6.44 (m, 2H), 3.64 (br s, 2H).

Example 16

2,4-Diiodo-phenylamine

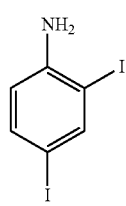

$^1$H NMR (400 MHz, CDCl$_3$) δ 7.87 (m, 1H), 7.35 (m, 1H), 6.47 (m, 1H), 4.12 (br s, 2H).

Example 17

1-(Bromomethyl)benzene

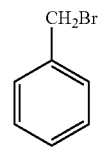

$^1$H NMR (400 MHz, CDCl$_3$) δ 7.34 (m, 5H), 4.49 (s, 2H).

Example 18

1-(Dibromomethyl)benzene

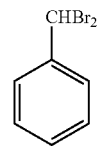

$^1$H NMR (500 MHz, CDCl$_3$) δ 7.57 (m, 2H), 7.35 (m, 3H), 6.64 (s, 1H).

Example 19

1-(Tribromomethyl)benzene

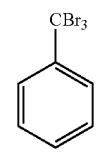

$^1$H NMR (400 MHz, CDCl$_3$) δ 8.00 (d, 2H, J=8.0 Hz), 7.34 (m, 3H).

Example 20

1-(1-Bromoethyl)benzene

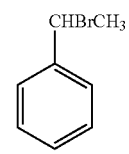

$^1$H NMR (400 MHz, CDCl$_3$) δ 7.42 (m, 2H), 7.32 (m, 3H), 5.20 (q, 1H, J=6.9 Hz), 2.03 (d, 3H, J=6.9 Hz).

Example 21

1-(Bromomethyl)naphthalene

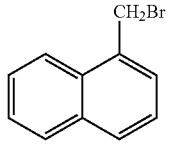

$^1$H NMR (400 MHz, CDCl$_3$) δ 8.11 (d, 1H, J=8.5 Hz), 7.80 (m, 2H), 7.57 (dt, 1H, J=1.4, 8.5 Hz), 7.48 (m, 2H), 7.34 (t, 1H, J=7.7 Hz), 4.90 (s, 2H).

Example 22

2-(Bromomethyl)naphthalene

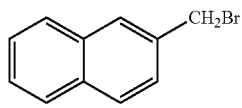

$^1$H NMR (400 MHz, CDCl$_3$) δ 7.76 (m, 4H), 7.44 (m, 3H), 4.60 (s, 2H).

Example 23

1-Bromo-2-(bromomethyl)benzene

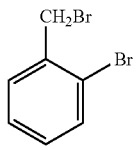

$^1$H NMR (500 MHz, CDCl$_3$) δ 7.56 (m, 1H), 7.44 (m, 1H), 7.28 (m, 1H), 7.15 (m, 1H), 4.59 (s, 2H).

Example 24

4-(Bromomethyl)-1,2-dichlorobenzene

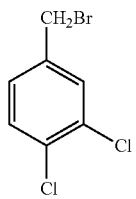

$^1$H NMR (400 MHz, CDCl$_3$) δ 7.47 (d, 1H, J=2.1 Hz), 7.39 (d, 1H, J=8.2 Hz), 7.21 (dd, 1H, J=2.1, 8.2 Hz), 4.40 (s, 2H).

Example 25

4-(Bromomethyl)-1,2-difluorobenzene

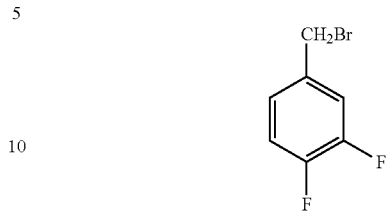

$^1$H NMR (400 MHz, CDCl$_3$) δ 7.22 (m, 1H), 7.12 (m, 2H), 4.42 (s, 2H).

Example 26

General Procedure for Halogenation of Materials Comprising Aromatic Compounds

A suspension of the material comprising an aromatic compound (1.0 g), NBS (0.5 g) and ZrCl$_4$ (0.0196 g, 3 mol %) in CH$_2$Cl$_2$ (5 mL) was stirred at room temperature under a N$_2$ atmosphere for 24 h. The solid was separated by filtration and washed well with CH$_2$Cl$_2$, then dried under vacuum. The weight % of halogen incorporation is determined by elemental analysis.

Example 27

Bromination of Graphite

A suspension of graphite (1.0 g), NBS (0.5 g) and ZrCl$_4$ (0.0196 g, 3 mol %) in CH$_2$Cl$_2$ (5 mL) was stirred at room temperature under a N$_2$ atmosphere for 24 h. The solid was separated by filtration and washed well with CH$_2$Cl$_2$, then dried under vacuum to afford brominated graphite. Weight % Br was determined by elemental analysis.

Example 28

Bromination of Charcoal

The procedure of example 27 was followed except that graphite was replaced by charcoal. Brominated charcoal (1.14 g) was isolated. Weight % Br determined by elemental analysis: 12.25%.

Example 29

Pyridine-3-graphite

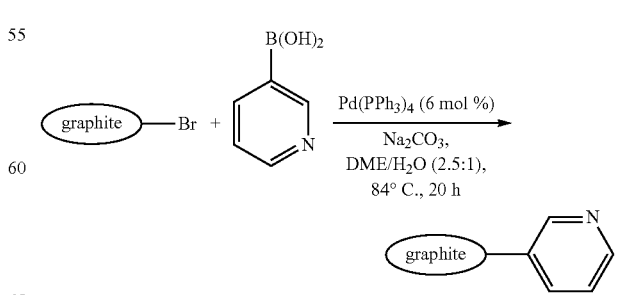

To a solution of brominated graphite (1.0 g) and pyridine-3-boronic acid (1 eq., according to weight % Br of brominated graphite) in 1,2-dimethoxyethane (3 mL) under nitrogen was added a solution of $Na_2CO_3$ (6 eq.) in water, followed by $Pd(PPh_3)_4$ (6 mol %). The reaction was stirred at 84° C. for 20 h. After cooling to room temperature, the suspension was filtered, and the solid was washed well with water and $CH_2Cl_2$, then dried under vacuum to afford 1.0 g of a black solid. Weight % N as determined by elemental analysis: 0.18%.

Example 30

(Pyridin-2-yl)pyridin-4-yl-4-graphite

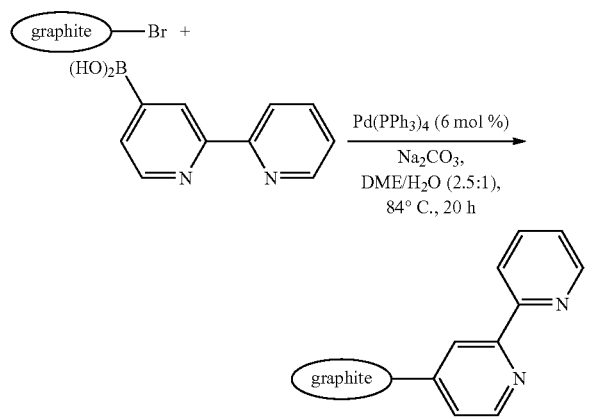

To a solution of brominated graphite (1.0 g) and (pyridin-2-yl)pyridin-4-yl-4-boronic acid (1 eq., according to weight % Br of brominated graphite) in 1,2-dimethoxyethane (3 mL) under nitrogen was added a solution of $Na_2CO_3$ (6 eq.) in water, followed by $Pd(PPh_3)_4$ (6 mol %). The reaction was stirred at 84° C. for 20 h. After cooling to room temperature, the suspension was filtered, and the solid was washed well with water and $CH_2Cl_2$, then dried under vacuum to afford 1.01 g of a black solid. Weight % N as determined by elemental analysis: 0.28%.

Example 31

$Pd(OAc)_2$(pyridine-3-graphite)$_2$

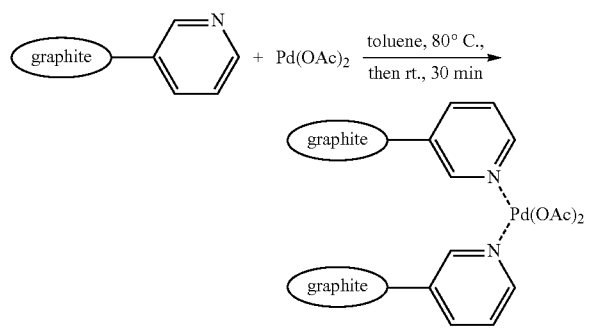

To a solution of $Pd(OAc)_2$ (0.5 eq., according to weight % N of graphite) in toluene (2 mL) at 80° C. was added pyridine-3-graphite (1.0 g) under nitrogen. The reaction was stirred at room temperature for 30 min. The solvent was removed slowly under vacuum to afford the desired catalyst.

Example 32

$Pd(OAc)_2$((pyridin-2-yl)pyridin-4-yl-4-graphite)

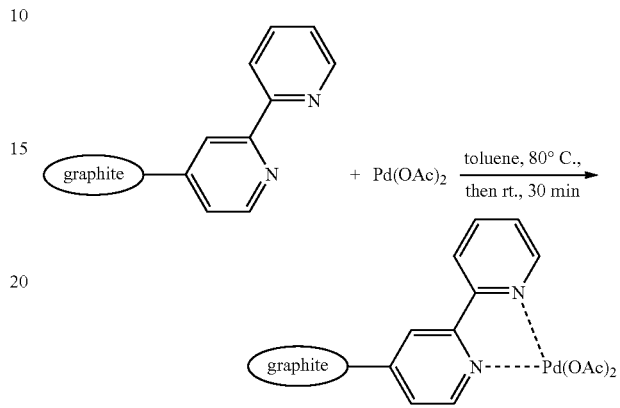

To a solution of $Pd(OAc)_2$ (1 eq., according to weight % N of graphite) in toluene (2 mL) at 80° C. was added (pyridin-2-yl)pyridin-4-yl-4-graphite (1.0 g) under nitrogen. The reaction was stirred at room temperature for 30 min. The solvent was removed slowly under vacuum to afford the desired catalyst.

Example 33

General Procedure for Oxidation of Alcohols

Under an air balloon, a solution of the Pd catalyst from Example 31 or 32 (0.3-0.5 mole %) and NaOAc (0.2 mmol) in toluene (2 mL) was stirred at room temperature for 1 min and at 80° C. for 3 min. Then the alcohol (2.0 mmol) was added over 1 min at 80° C., and the solution was stirred at 80° C. for the time listed in Table 10-11 After the mixture was cooled to room temperature, the catalyst was filtered off, and the filtrate was concentrated under reduced pressure to afford the desired alcohol or ketone. The yield of the reaction was determined by $^1$H NMR.

Example 34

(Bromomethyl)trimethylsilane

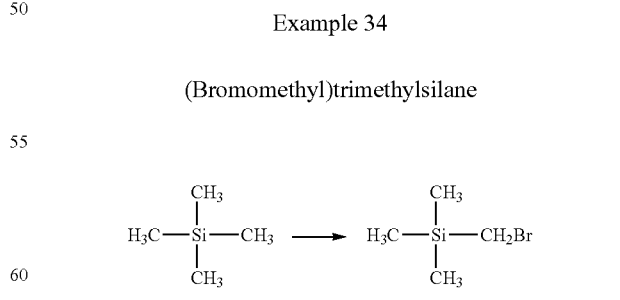

To a suspension of NBS (50 mmol) and $AlCl_3$ (5 mol %) in $CH_2Cl_2$ (400 mL) was added $Me_4Si$ (50 mmol) under nitrogen. The solution was stirred at room temperature for 18 h. The reaction was quenched by a saturated aqueous solution of $NaHCO_3$, and the separated organic phase was washed with brine. After drying over Na$_2$SO$_4$, the organic phase was distilled and (bromomethyl)trimethylsilane was obtained as major product.

Example 35

(1,1-Dibromoethyl)triethylsilane

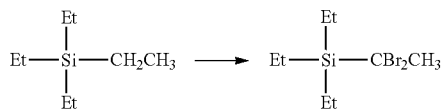

To a suspension of NBS (60 mmol) and ZrCl$_4$ (5 mol %) in CH$_2$Cl$_2$ (240 mL) was added Et$_4$Si (30 mmol) under nitrogen. The solution was stirred at room temperature for 18 h. The reaction was quenched by a saturated aqueous solution of NaHCO$_3$, and the separated organic phase was washed with brine. After drying over Na$_2$SO$_4$, the organic phase was concentrated in vacuum, and the crude product was distilled to give (1,1-dibromoethyl)triethylsilane.

It is therefore intended that the foregoing detailed description be regarded as illustrative rather than limiting, and that it be understood that it is the following claims, including all equivalents, that are intended to define the spirit and scope of this invention.

The invention claimed is:

1. A method of halogenating an activated carbon atom in the presence of a Lewis acid comprising,
   reacting a material comprising an activated carbon atom with a halogen donor in the presence of a catalytic amount of the Lewis acid; wherein the Lewis acid comprises a metal selected from the group consisting of Zr, Fe, and Al;
   wherein the activated carbon atom is a carbon atom alpha to a silicon atom and the material is represented by formula VIIa:

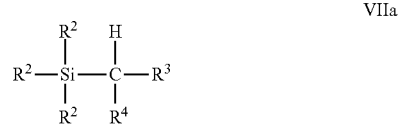

wherein
   R$^2$ is independently selected from the group consisting of hydrogen, —OR$_3$, —NR$^3$R$^4$, —SR$^3$, C$_{1-8}$ alkyl, C$_{1-8}$ heteroalkyl, C$_{1-8}$ haloalkyl, C$_{2-8}$ alkenyl, C$_{2-8}$ alkynyl, 3- to 10-membered heterocyclyl, C$_{6-10}$ aryl, and 5- to 10-membered heteroaryl; and
   R$^3$ and R$^4$ an each independently selected from the group consisting of hydrogen, C$_{1-8}$ alkyl, C$_{1-8}$ heteroalkyl, C$_{2-8}$ alkenyl, C$_{2-8}$ alkynyl, C$_{6-10}$ aryl, 5 to 10-membered heteroaryl, and 3- to 10-membered heterocycle; and
   wherein the halogen donor is selected from the group consisting of N-bromosuccinimide, N-iodosuccinimide, N-chlorosuccinimide and N-fluorobenzene-sulfonimide.

2. The method of claim 1, wherein the Lewis acid comprises Zr.

3. The method of claim 2, wherein the Lewis acid is ZrCl$_4$.

* * * * *

UNITED STATES PATENT AND TRADEMARK OFFICE
CERTIFICATE OF CORRECTION

PATENT NO.        : 8,618,320 B2
APPLICATION NO.   : 13/404364
DATED             : December 31, 2013
INVENTOR(S)       : Yanhua Zhang et al.

It is certified that error appears in the above-identified patent and that said Letters Patent is hereby corrected as shown below:

In the Claims

In claim 1, column 46,
    line 22, after "$R^3$ and $R^4$" delete "an" and insert therefore --are--; and
    line 24, delete "5 to 10-membered" and insert therefore --5- to 10-membered--.

Signed and Sealed this
Twenty-seventh Day of May, 2014

Michelle K. Lee
*Deputy Director of the United States Patent and Trademark Office*